(12) United States Patent
Brugger et al.

(10) Patent No.: US 11,679,190 B2
(45) Date of Patent: Jun. 20, 2023

(54) BLOOD TREATMENT DEVICE PRIMING DEVICES, METHODS, AND SYSTEMS

(71) Applicant: NxStage Medical, Inc., Lawrence, MA (US)

(72) Inventors: James M. Brugger, Newburyport, MA (US); David Desouza, Essex, MA (US)

(73) Assignee: NxStage Medical, Inc., Lawrence, MA (US)

( * ) Notice: Subject to any disclaimer, the term of this patent is extended or adjusted under 35 U.S.C. 154(b) by 212 days.

(21) Appl. No.: 17/218,860

(22) Filed: Mar. 31, 2021

(65) Prior Publication Data

US 2021/0213191 A1 Jul. 15, 2021

Related U.S. Application Data

(62) Division of application No. 16/366,714, filed on Mar. 27, 2019, now Pat. No. 10,987,461, which is a
(Continued)

(51) Int. Cl.
*A61M 1/36* (2006.01)
*A61M 39/10* (2006.01)

(52) U.S. Cl.
CPC ........ *A61M 1/3643* (2013.01); *A61M 1/3629* (2014.02); *A61M 1/3644* (2014.02);
(Continued)

(58) Field of Classification Search
CPC .............. A61M 1/3629; A61M 1/3643; A61M 1/3644; A61M 1/3646; A61M 1/3652; A61M 1/3672; A61M 39/10; A61M 2205/3331; A61M 2205/702; A61M 2205/705; A61M 2205/707
See application file for complete search history.

(56) References Cited

U.S. PATENT DOCUMENTS 4,108,764 A 8/1978 Kaneko et al.
5,951,870 A 9/1999 Utterberg
(Continued)

FOREIGN PATENT DOCUMENTS

CA 2052523 3/1999
CA 2219820 8/2006
(Continued)

OTHER PUBLICATIONS

Extended European Search Report dated Jun. 20, 2022 for European Patent Application No. 22158470.9.
(Continued)

*Primary Examiner* — John Kim
(74) *Attorney, Agent, or Firm* — Potomac Law Group, PLLC

(57) ABSTRACT

Simple-to-use systems, methods, and devices for priming replacement blood treatment devices, for swapping the blood treatment devices out, for replacing swapped-out blood treatment devices, and other related operations are described. In embodiments, a blood treatment device can be primed while a therapy is still running. When the replacement blood treatment device is needed, the therapy can be stopped momentarily (less than a minute) for the rapid and safe swap of the blood treatment device. Blood loss can be minimized. The down time from therapy can be minimized.

13 Claims, 14 Drawing Sheets

Related U.S. Application Data division of application No. 15/564,719, filed as application No. PCT/US2016/026525 on Apr. 7, 2016, now Pat. No. 10,279,098.

(60) Provisional application No. 62/298,620, filed on Feb. 23, 2016, provisional application No. 62/143,880, filed on Apr. 7, 2015.

(52) U.S. Cl.
CPC ........ *A61M 1/3646* (2014.02); *A61M 1/3652* (2014.02); *A61M 1/3672* (2013.01); *A61M 39/10* (2013.01); *A61M 2205/3331* (2013.01); *A61M 2205/702* (2013.01); *A61M 2205/705* (2013.01); *A61M 2205/707* (2013.01)

(56) References Cited

U.S. PATENT DOCUMENTS

| | | |
|---|---|---|
| 5,954,957 A | 9/1999 | Chin-Loy et al. |
| 6,387,069 B1 | 5/2002 | Utterberg |
| 7,588,722 B2 | 9/2009 | Chevallet |
| 7,686,778 B2 | 3/2010 | Burbank et al. |
| 8,523,799 B2 | 9/2013 | Biesel et al. |
| 8,875,748 B2 | 11/2014 | Beden et al. |
| 8,877,063 B2 | 11/2014 | Kawarabata et al. |
| 2006/0102091 A1 | 5/2006 | Kissinger |
| 2007/0179422 A1 | 8/2007 | Schnell et al. |
| 2007/0185430 A1 | 8/2007 | Brugger et al. |
| 2008/0214981 A1 | 9/2008 | Delnevo et al. |
| 2009/0312686 A1 | 12/2009 | Sakamoto et al. |
| 2012/0298580 A1 | 11/2012 | Gronau et al. |
| 2012/0325696 A1 | 12/2012 | Burbank et al. |
| 2013/0025357 A1 | 1/2013 | Noack et al. |
| 2015/0135804 A1 | 5/2015 | Rovatti et al. |
| 2015/0367062 A1 | 12/2015 | Brugger et al. |
| 2017/0021086 A1 | 1/2017 | Lura et al. |
| 2017/0224902 A1 | 8/2017 | Wojke et al. |
| 2017/0232179 A1 | 8/2017 | Wojke et al. |

FOREIGN PATENT DOCUMENTS

| | | |
|---|---|---|
| EP | 0090093 B1 | 6/1988 |
| EP | 1632264 A2 | 3/2006 |
| EP | 2583700 A1 | 4/2013 |
| EP | 2468324 B1 | 4/2014 |
| EP | 2397168 B1 | 5/2014 |
| EP | 2609944 B1 | 1/2015 |
| JP | H0910303 A | 1/1997 |
| JP | 2001348060 A | 12/2001 |
| JP | 2002193326 A | 7/2002 |
| JP | 2006094934 A | 4/2006 |
| JP | 2006282237 A | 10/2006 |
| JP | 2010000161 A | 1/2010 |
| JP | 2011015877 A | 1/2011 |
| JP | 2011182992 A | 9/2011 |
| JP | 5160975 B2 | 3/2013 |
| JP | 5243097 B2 | 7/2013 |
| JP | 5276909 B2 | 8/2013 |
| JP | 5539845 B2 | 7/2014 |
| JP | 2016036534 A | 3/2016 |
| JP | 2016036535 A | 3/2016 |
| JP | 2016083003 A | 5/2016 |
| JP | 5985224 B2 | 9/2016 |
| JP | 5053107 B2 | 12/2016 |
| WO | 2010042666 A2 | 4/2010 |
| WO | 2011118411 A1 | 9/2011 |
| WO | 2013183599 A1 | 12/2013 |
| WO | 2014050468 A1 | 4/2014 |
| WO | 2014124180 A2 | 8/2014 |
| WO | 2014124180 A3 | 10/2014 |
| WO | 2016171180 A1 | 10/2016 |
| WO | 2016198841 A1 | 12/2016 |
| WO | 2017016662 A1 | 2/2017 |
| WO | 2017069171 A1 | 4/2017 |

OTHER PUBLICATIONS

Extended search report that issued in the corresponding EP Application No. 16777313.4, dated Oct. 30, 2018.
International Preliminary Report on Patentability for International Patent Application No. PCT/US2016/026525 dated Oct. 10, 2017.
International Search Report and Written Opinion for International Patent Application No. PCT/US2016/026525 dated Sep. 6, 2016.
Office Action (Notice of Reason for Rejection) dated Jan. 21, 2020 for Japanese Patent Application No. 2017-553025.
Office Action (Notice of Reason for Rejection) dated Jun. 30, 2020 for Japanese Patent Application No. 2017-553025.
Office Action (Notice of Reasons for Refusal) dated Jul. 30, 2019 for Japanese Patent Application No. 2017-553025.

BLOOD TREATMENT DEVICE PRIMING DEVICES, METHODS, AND SYSTEMS

CROSS-REFERENCE TO RELATED APPLICATIONS

This application is a Divisional of U.S. patent application Ser. No. 16/366,714 filed Mar. 27, 2019, now U.S. Pat. No. 10,987,461, which is a Divisional of U.S. patent application Ser. No. 15/564,719 filed Oct. 5, 2017, (now U.S. Pat. No. 10,279,098), which claims priority under 35 U.S.C. § 371 to International Application No. PCT/US2016/026525 filed Apr. 7, 2016, which claims the benefit of U.S. Provisional Application Nos. 62/298,620 filed Feb. 23, 2016 and 62/143,880 filed Apr. 7, 2015, all of which are hereby incorporated by reference in their entireties.

REFERENCE TO GOVERNMENT GRANT

This invention was made with Government support under Contract No. HR0011-13-C-0023 awarded by Defense Advanced Research Projects Agency (DARPA). The Government has certain rights in this invention.

FIELD

The present disclosure relates generally to blood treatment devices for a bodily fluid, and, more particularly, to systems, methods, and devices for priming of a bodily fluid treatment device, such as a blood treatment device.

BACKGROUND

Dialysis and other forms of blood treatment employ blood treatment devices that are used to remove water and/or other undesired constituents from the blood and restore can also help electrolytes to the blood of patients. Dialyzers, a type of blood treatment device, for example, can replace the natural function of the kidney. In dialysis blood is treated outside of the body of the patient by passing it through a dialyzer. Hemoperfusion is another type of treatment that uses blood treatment devices. Regardless of the type of treatment, a problem with using treatment devices such as blood treatment devices and dialyzers is the presence of air or other gas or gasses in the blood treatment device prior to connection to a patient. If air or other gas or gasses and/or bubbles are present in the blood treatment device, the patient may be injured by air or other gas or gasses embolisms or clot embolisms induced by the air or other gas or gasses in the blood treatment device and tubing. Priming with fluid such as saline is used to remove air or other gas or gasses. Priming techniques on dialysis blood lines and blood treatment devices includes pumping the priming fluid through the circuit, hammering, inverting, and shaking the blood treatment device while flowing fluid through it in order to remove the air or other gas or gasses and/or bubbles. Automated systems that can be used for priming are also known, but they can inconvenient if it is desired to prime a blood treatment device to permit it to stand by for replacement in a system being used for treatment. Also existing automated systems may tie up the treatment system or be complex. Dialyzers and other blood treatment devices are commonly sold as standalone products and have labeling that prescribes the amount of saline that must be used to prime. The users are obliged to follow these instructions, making replacing a blood treatment device during a therapy session very difficult, if not impossible since blood is already in the blood tubing circuit and in the blood treatment device to be replaced. Also, many Continuous Renal Replacement Therapy (CRRT) machines have a preconnected and bonded in place blood treatment device, making replacement of the blood treatment device impossible. The CRRT disposable consists of a blood treatment device, a blood line portion and a therapy fluid portion. During a therapy session, sometimes the blood treatment device becomes exhausted and clogged, but the rest of the disposable circuit is still useable. An option is to discard the entire circuit. This takes therapy time away from the patient as the circuit is swapped, primed, and tested prior to reinitiating the therapy, and a substantial portion of the disposable cost is the non-blood treatment device portion.

SUMMARY

Simple-to-use systems, methods, and devices for priming replacement blood treatment devices, for swapping the blood treatment devices out, for replacing swapped-out blood treatment devices, and other related operations are described. In embodiments, a blood treatment device can be primed while a therapy is still running. When the replacement blood treatment device is needed, the therapy can be stopped momentarily (less than a minute) for the rapid and safe swap of the blood treatment device. Blood loss can be minimized. The down time from therapy can be minimized.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

DESCRIPTION

Figure 1:
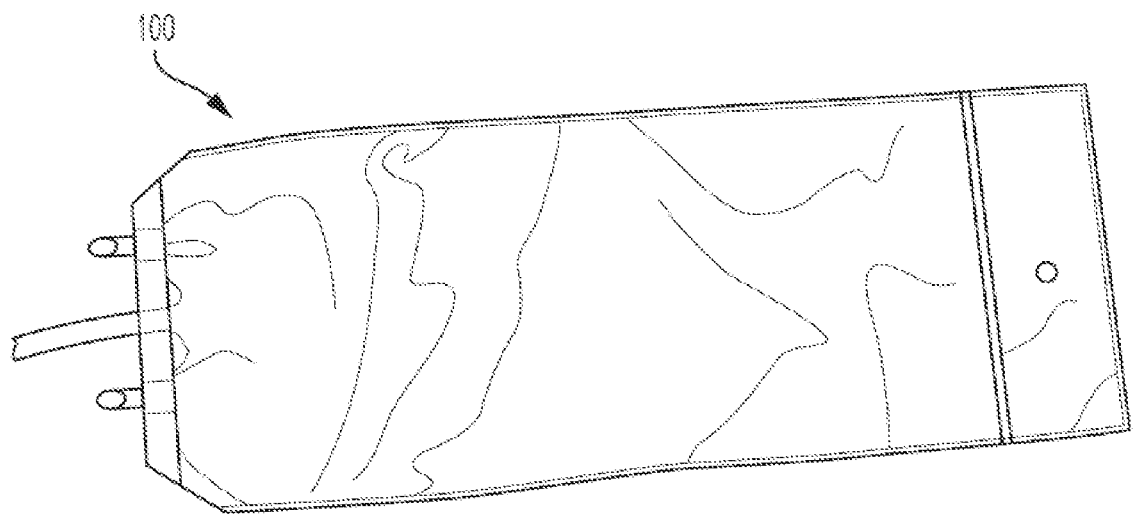
FIG. 1 is an image of a drain bag, according to one or more embodiments of the disclosed subject matter.

Blood treatment devices must be primed with a physiologic fluid like saline in order to use them in a blood circuit. With some of the devices, methods, and systems according to the currently disclosed subject matter, blood treatment devices can be swapped out when the physician or medical staff determine the useful life has exhausted. In certain types of treatments, it may be advantageous for blood treatment devices to be primed and ready to replace in a blood circuit, for example, to replace ones currently being used if they become clogged or ineffective.

Priming a blood treatment device can be an attention-consuming process because it needs to be done in a way that prevents air or other gas or gasses from entering the circuit. Priming replaces air or other gas or gasses in the blood treatment device with physiological fluid, for example, a blood normal saline solution or a bio-compatible fluid, in preparation for blood flowing through the blood treatment device. This is at least partly due to the fact that air or other gas or gasses contact with blood creates a risk of clotting. Priming also flushes away impurities in the blood treatment device. Impurities can exist because of residual sterilization chemicals (e.g., ethylene oxide), chemicals used in manufacturing, or particulates from the manufacture of the blood treatment device. Priming can also activate a component of the blood treatment device allowing it to perform its specific therapy when in contact with blood. Priming of the blood circuit and blood treatment device is a common practice in dialysis and other blood processing therapies. After priming, the blood circuit and/or blood treatment device can be subject to flushing, which refers to rinsing additional fluid through the primed blood treatment device.

There are many different types of blood treatment devices that may be used in blood processing therapies such as perfusion, sepsis therapy, therapeutic plasma exchange, and other similar types of therapy. Different blood treatment devices have some common requirements and some that differ according to the type or manufacturer. One of the differences is whether the priming solution can be given to a patient, or must be flushed from the blood treatment device, prior to use.

In one priming procedure, a bag of fluid is spiked to allow gravity flow into a blood treatment device to be primed. Fluid exiting the blood treatment device was sometimes captured in a drain bag. The priming of blood treatment devices may require the user to watch the process in order to stop the saline flow before the saline bag empties, lest air or other gas or gasses enter the blood treatment device. If the user gets distracted, the saline bag could empty, pulling air or other gas or gasses into the just-primed blood treatment device. This requires, at a minimum, that the priming process be redone in order to remove this newly introduced air or other gas or gasses prior to connection of the blood treatment device to the patient. With many blood treatment devices re-priming is not possible, because once the internal material is wetted and then air or other gas or gasses is introduced, the air or other gas or gasses attaches to the material due to surface tension which reduces the effective surface area of the blood treatment device and results in periodic venting of air or other gas or gasses into the blood line.

According to one or more embodiments of the disclosed subject matter, a better priming procedure and apparatus can provide for flushing the blood treatment device separately from the blood processing machine using, for example, an ancillary disposable blood treatment device priming set. In an embodiment of a blood treatment device priming set, an assembly includes tubing with a bag spike and a drain bag of a predefined configuration. The described blood treatment device priming set and method of use allow for error proof priming by stopping the saline automatically prior to the emptying of the saline bag by employing a drain bag whose volume is selected to keep air or other gas or gasses from entering the blood treatment device. In embodiments, this drain bag maximum volume is less than a total volume of the priming fluid. In further embodiments, this drain bag maximum volume is less than a total volume of the priming fluid plus the volume of the blood treatment device plus the volume of the priming circuit downstream of the blood treatment device. The purpose of the drain bag is to capture the saline that is gravity fed through the blood treatment device and to stop the flow once the bag has reached its fill capacity. This also captures the used saline, which is now considered waste, for easy and convenient disposal. In embodiments, the condition can be ensured by ensuring that a source container, such as a bag, cannot drain fully, maintaining a fluid "head" above the level of the blood treatment device being primed by gravity flow. In further embodiments, the volume may be less, but at least the possibility that the fluid flow through the blood treatment device may draw air or other gas or gasses into the blood treatment device is eliminated. Note that in alternative embodiments, if a sealed priming circuit can be assured, the drain container can have a larger volume than the embodiments described above if the flow of fluid can be halted by a vacuum on the supply side of the priming circuit. For example, if air or other gas or gasses is eliminated from a container of priming fluid and the priming circuit, the fluid can drain from it until a negative pressure develops in the priming fluid container. The negative pressure may be generated by the collapse of the priming fluid container and/or simply result from the draw-down of fluid in the case where the priming fluid container is a rigid container that. Both may have the effect of shutting down the siphon head of the priming circuit. Any of the features of the device, system, and method embodiment disclosed herein may be employed in such an embodiment. Effectively, the flow of the priming circuit here is halted by a negative pressure generated upstream rather than a positive pressure downstream.

The bag spike allows for the connection of the priming set to commonly-used priming solution bags. In general, normal saline is the priming solution of choice and these bags are typically 1 liter in volume. In an example, the blood treatment device priming set will have 2 bag spikes for 2 bags of saline for a 2 liter prime and flush. Alternatively, the blood treatment device priming set can have one spike for a 1 liter prime and flush. In yet another alternative, the blood treatment device priming set can have 3 spikes for a 3 liter prime and flush, in order to allow for greater priming volumes. Other numbers of spikes and volumes for priming and flushing are also possible according to one or more contemplated embodiments.

The drain bag of the priming set can be of a material selected to ensure that any stretching that may occur at predefined temperatures is insufficient to prevent the arrest of the flow that ensures that air or other gas or gasses cannot enter the blood treatment device. For example, it is known that flexible PVC bags can stretch to large sizes with very little pressure due to the large surface area of the bag. An image of an exemplary drain bag 100 is shown in FIG. 1. Common PVC drain bags may stretch and not perform as intended. In contrast, the drain bag according to one or more embodiments of the disclosed subject matter is less elastic than PVC. In further embodiments, the drain bag can be inelastic. For example, the drain bag is of a multilayer film with high tensile rigidity layer or layers. In still further embodiments, a heat-welded bag made of a nylon outer layer and a polyethylene inner layer may be employed. The thickness is generally between 1 and 6 mil, but generally 3 to 4 mil. Alternatively, or additionally, the drain bag can be placed in a rigid support, such as a tank or a non-expandable pouch that prevents a drain bag of elastic material from expanding. The latter can be a reusable component attached to a blood treatment machine.

Figure 2:
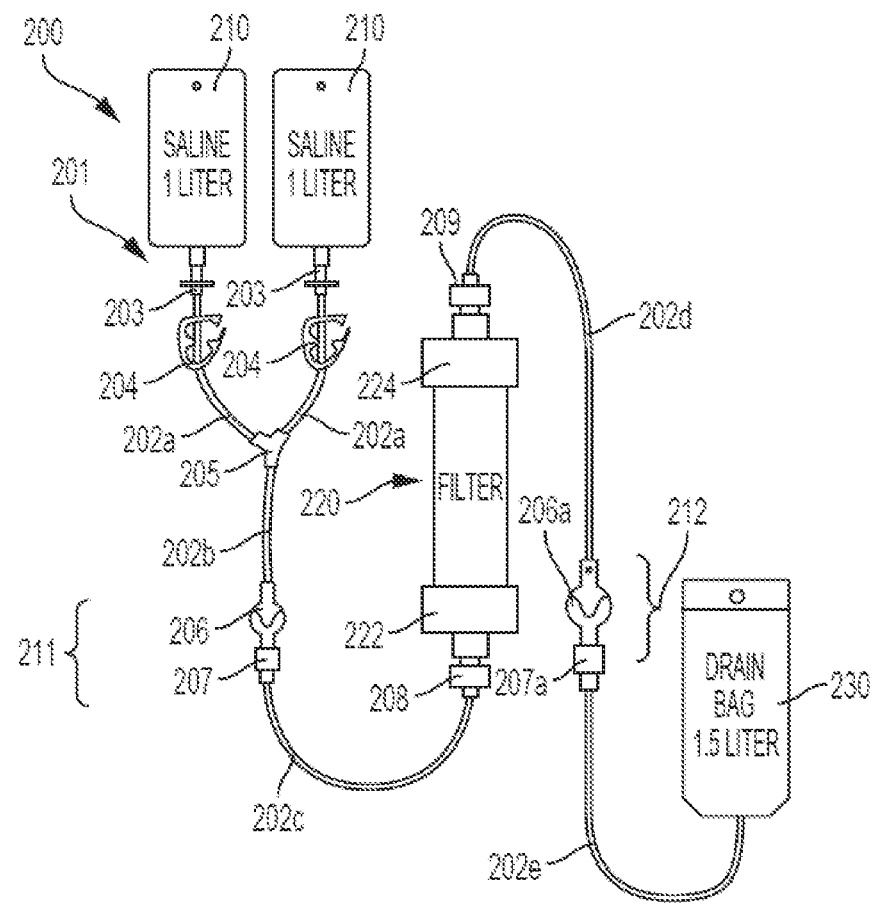
FIG. 2 is a drawing of a setup for priming, according to one or more embodiments of the disclosed subject matter.

In another example of a blood treatment device priming set 201 of a priming setup 200, as shown in FIG. 2, with the blood treatment device priming set 201 includes 2 bag spikes 203 and a drain bag 230 has a capacity of 1.5 liters, which is more than the priming volume of a blood treatment device 220, the priming volume of the blood treatment device priming set 201. In the priming fluid circuit 200, multiple saline bags 210 are hung a height above a blood treatment device 220, which in turn is mounted above a drain bag 230. The vertical elevation difference between the saline bags 210 and the drain bag 230 can generate a siphon effect that draws fluid through the blood treatment device 220. The elevation difference may be used to select the speed at which the blood treatment device 220 is primed. Also the tubing diameters can be used to select speed of priming. Note that as used here, priming may also include flushing in that more than a quantity merely sufficient for filling the fluid may flow through the priming circuit 200 in order to purge air or other gas or gasses and undesirable materials such as manufacturing residuals from the blood treatment device 220. The vertical elevations can be optimized for the variety of blood treatment devices anticipated to be used and to allow for a prime of each type of blood treatment device within a predefined period of time.

Figure 3A:
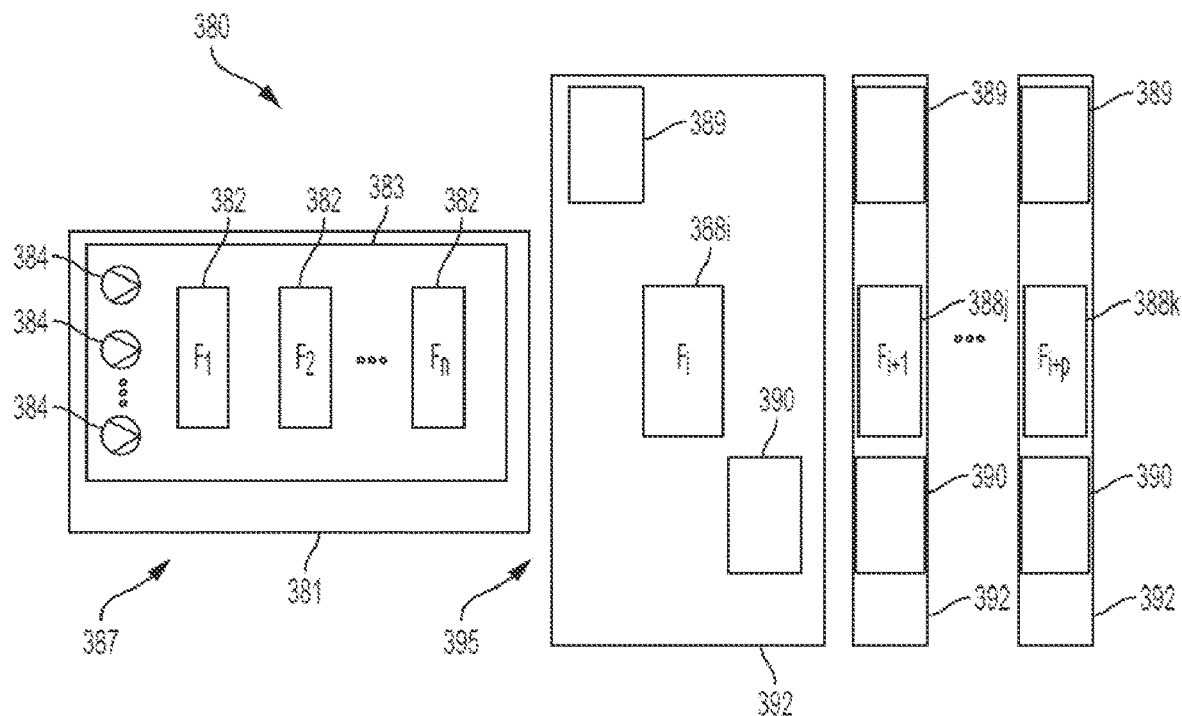
FIGS. 3A and 3B show respective drawings of systems that may support and/or employ the blood treatment device swapping system and method, according to one or more embodiments of the disclosed subject matter.
Figure 3B:
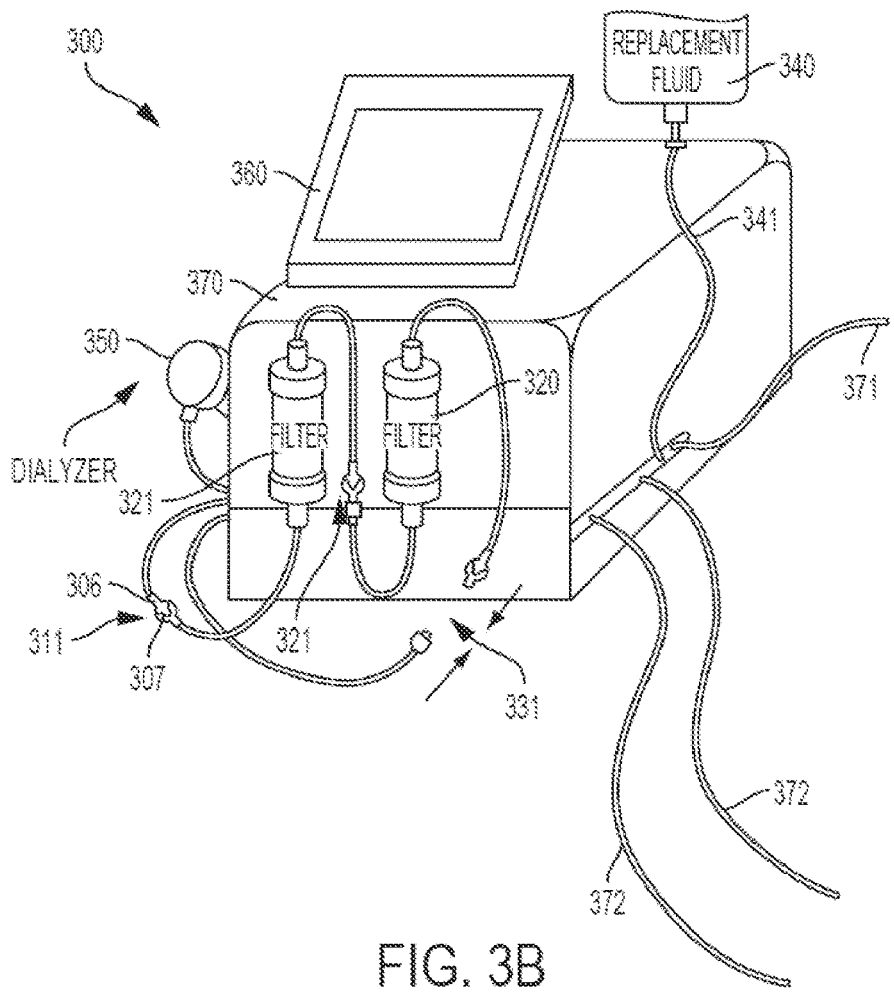

In the illustration of the two bag spike example in FIG. 2, the two bags of saline 210 are hung, for example, on an IV pole or equivalent support, and spiked so that the saline flows into tubing 202a-202c that connected to output ends of the bag spikes 203. The tube lengths 202a join at a Y-junction 205. Flow from the bags of saline 210 flows to an arterial blood circuit connector of the blood treatment device 208 (the nomenclature arterial blood circuit applies to dialysis and hemofiltration blood treatment devices but other types of blood treatment devices may be primed using the devices and method described), fills the blood treatment device 220, exits the blood treatment device through a venous connector 209, then flows through a drain line 202d, 202e to a drain container (bag) 230. The dialyzer may be held in a holder that orients it such that the saline flows from bottom to top. This flow direction helps to eliminate air or other gas or gasses by exploiting buoyancy. The drain bag may be hung at a location below that of the saline bags. The saline flows through the blood treatment device 220 and into the drain bag 230 until the drain bag 230 has reached its capacity, whereupon the flow stops automatically due to the stiffness of the drain bag 230 and the predefined volume thereof. Once the blood treatment device 220 is primed (flushed as well), the blood treatment device and the tube lengths 202c and 202d as well as male 206a and female self-sealing 207 connectors can be disconnected, thereby self-sealing, and reconnected in a treatment circuit to replace a blood treatment device currently in use as illustrated in FIGS. 3A and 3B.

By halting the flow of priming fluid in the manner described, a blood treatment device 220 is primed in an unattended fashion. That is, the user performing the priming does not have to observe, and timely halt, the priming process in order to ensure that no air or other gas or gasses enters the blood treatment device 220. Ordinarily, the flow would be stopped by engaging a pair of pinch clamps 204 (or elsewhere to the same effect).

In embodiments, in addition to the gravity priming and automatic stopping of the priming process, a tubing set for priming blood treatment devices can include self-sealing connectors 211 that eliminate the need for pinch clamps by opening the fluid path upon connection and sealing fluid prior to connection or after disconnection. Such valves are available off the shelf, for example, but not limited to, Halkey-Roberts connectors 211, 212 which have a male connector half 206, 206a and a female connector half 207, 207a. Halkey Roberts self-sealing connectors are readily available on the market. However other self-sealing connectors could be employed or non-self-sealing connectors with manual tube clamps could be employed. As well, the use of self-sealing connectors is not required to take advantage of the easy priming technique. For example, but not limited to, standard male and female luer connections can be used, as well as any number of fluid connections available, such as DIN Connectors. Self-sealing connectors are particularly advantageous in hemoperfusion therapies with highly contagious diseases such as ebola or HIV. By making the sealing and closing off of the circuit automatic, there is less likelihood of contamination of the treatment environment and/or the medical staff.

In general, standard dialyzers and blood treatment devices employ dialyzer connectors that are the same at both ends of the dialyzer. This makes it possible to connect the dialyzer incorrectly. For a dialyzer to perform most efficiently there must be counter current flow of the blood relative to the dialysate flow. If the flows are parallel, then there is a loss in clearance of toxins through the membrane due to a reduced osmotic gradient. In a method according to one or more embodiments of the disclosed subject matter, immediately after an extracorporeal blood tubing set is primed, which can include after the patient has been connected, primed blood treatment devices that have been primed by the devices and methods disclosed, can be connected into a blood circuit 300 in a safe manner without blood loss, as illustrated by FIGS. 3A and 3B.

FIG. 3A shows a system 380 that employs and supports swapping of blood treatment devices. The system 380 includes one or more blood treatment device priming sets 395, each of which includes a fluid circuit 392 that interconnects a source container 389 with priming fluid, a blood treatment device 388, and a drain container 390. Each of the blood treatment devices 388i through 388k may be any type of treatment device and the one or more multiple blood treatment devices 388i through 388k may be of any of the types listed above. The fluid circuits 392 may be of any of the types described herein, preferably those embodiments that are effective for permitting unattended priming of a respective blood treatment device 388i through 388k.

FIG. 3B shows a treatment fluid circuit that includes blood treatment devices 320 and 321 as well as a dialyzer 350. The 320 and 321 as well as a dialyzer 350 may be any type of treatment device and may be any number. In an embodiment, there are multiple types, such as illustrated, where a patient may be treated for multiple conditions including renal failure, sepsis (removal of bacterial particles), or other conditions. The different types of treatment devices (illustrated by way of example by 320 and 321 as well as a dialyzer 350) may include hemofilter, dialyzers, apheresis blood treatment devices, adsorbent blood treatment devices, sepsis filter, and other types of treatment devices. This disclosed subject matter is applicable for the priming and use of new and yet to be developed blood treatment device technologies. By allowing the blood treatment device to be primed separately from the therapy machine and blood/therapy fluid disposable, the flexibility available to the physician increases. A review of priming requirements of various currently marketed blood treatment devices makes incorporating an automated priming sequence into a therapy machine difficult without constant software updates for each new blood treatment device type. Blood treatment devices 382 which may be of any type, including a mix of types, may be replaced by blood treatment devices 388i through 388k. Again, all the blood treatment devices illustrated in FIG. 3A and elsewhere are understood to be any type of treatment device as identified anywhere herein. The only limitation in terms of the unattended priming feature of the disclosed subject matter is that such treatment devices may benefit from, or require, priming and most preferably benefit from advance priming prior to installation on a fluid circuit.

FIG. 3B also shows further parts of the system 380 including a treatment system 387 that includes a treatment machine 381 that has pumps 384 and other elements that engage a fluid circuit 383. The fluid circuit 383, which may be disposable, interconnects one or more of the blood treatment devices 382, which again may be of different types from each other according to one or more treatments being provided. One or more of the blood treatment devices are replaceable with one or more of the blood treatment devices 388i through 388k. The fluid circuit 383 may interconnect the blood treatment devices 382 in any manner according to a type of treatment. Not shown, but possibly being present, is a patient who may be connected by the fluid circuit 383. The pumps 384 may be peristaltic pumps or any other type of pump. The fluid circuit 383 may include blood handling elements such as one or more of tubes, pressure pods, drip chambers, junctions, temperature sensors, pumping tube segments, and other elements of a blood handling fluid circuit. The treatment machine 381 may include temperature and pressure transducers, pump actuators, valve clamps, and other elements that may be employed in current or future types of treatment machines.

In an example system 300, illustrated in FIG. 3B, the blood treatment devices 320 and 321 may be sepsis filters. A treatment machine 370 has a display/control panel 360, a dialytic blood treatment device 350, sepsis filters 320 and 321 which are connected using self-sealing connectors 311, 321, 331 that convey blood being treated through the sepsis filters 320 and 321. A replacement fluid 340 may be provided through a line 341 and waste fluid drained through a line 371. Blood lines 372 may transfer blood to and from a patient.

In embodiments, it may be desirable to prime portions of a blood circuit separately from other parts. For example, sepsis filters may contain materials for storage and preservation or manufacturing products that must be cleansed from them prior to use. It may also be the case that it is undesirable for a priming fluid that is used to cleanse one sepsis filter to flow into another sepsis filter or other device. For example, that would be the case if the system of FIG. 3B were primed in the common manner of flowing priming fluid through the entire treatment circuit prior to performing the treatment. This may result in priming fluid causing cross-contamination, in effect, or increasing the volume of fluid required to fully remove the materials to be washed out. Also some blood treatment devices may not be compatible with the materials being purged from other blood treatment devices. In such cases, some or all the blood treatment devices in a single circuit may be primed individually according to the disclosed methods above and below and using the devices described. So this is an additional function provided by the disclosed priming devices, methods and systems.

During a treatment procedure, the treatment system 387 may be observed by an operator who may identify a need for the change of any of the one or more blood treatment devices 382. Upon an identification of a need to change the any of the one or more blood treatment devices 382, the user may set up any one or more of the one or more fluid circuits 392 for unattended priming of one or more corresponding blood treatment devices 388i through 388k and then prime it/them.

In a method embodiment, blood treatment device 320 is replaced by another, such as blood treatment device 220 of FIG. 2, which has previously been primed as discussed with reference to FIG. 2. To do this, self-sealing connectors 211 and 212 of FIG. 2 are separated isolating a priming fluid volume in the blood treatment device 220 and the lines 202c and 202d and making accessible the female connector 207 and male connector 206a of the self-sealing connectors 211 and 212. Corresponding self-sealing connectors 321 and 331 (FIG. 3B) may then be separated and the self-sealing connectors 211 and 212 mated to the corresponding male and female connectors mated to replace blood treatment device 320.

Embodiments may employ self-sealing connectors or regular connectors with clamps. With self-sealing connectors 311, 321, 331, there is a reduced risk of loss of fluid from the primed blood treatment device or loss of blood from the receiving fluid circuit when the disconnection is made. Then when lines are connected (by making the self-sealing connector connections), the connections open up allowing flow of the fluid or blood.

It is noted that the type of blood treatment device or other device primed using the devices and methods above may be varied. In addition to the above-described sepsis filters, embodiments of the disclosed technique are applicable to dialyzers, hemofilters, perfusion blood treatment devices, therapeutic plasma exchange blood treatment devices and other devices that need to be primed prior to being connected to an extracorporeal blood tubing set for blood delivery to a blood treatment device and return to a patient.

In order to facilitate interchangeability of various types of blood treatment devices using the described methods and devices, it may be important to have consistent connection types within a given product line, which, for example in this case, the male connector will always point in the direction of the intended fluid flow. This will ensure that the resulting primed blood treatment device or blood treatment devices will be connected properly. It also allows for multiple blood treatment devices to be connected in series, if desired.

Figure 4:
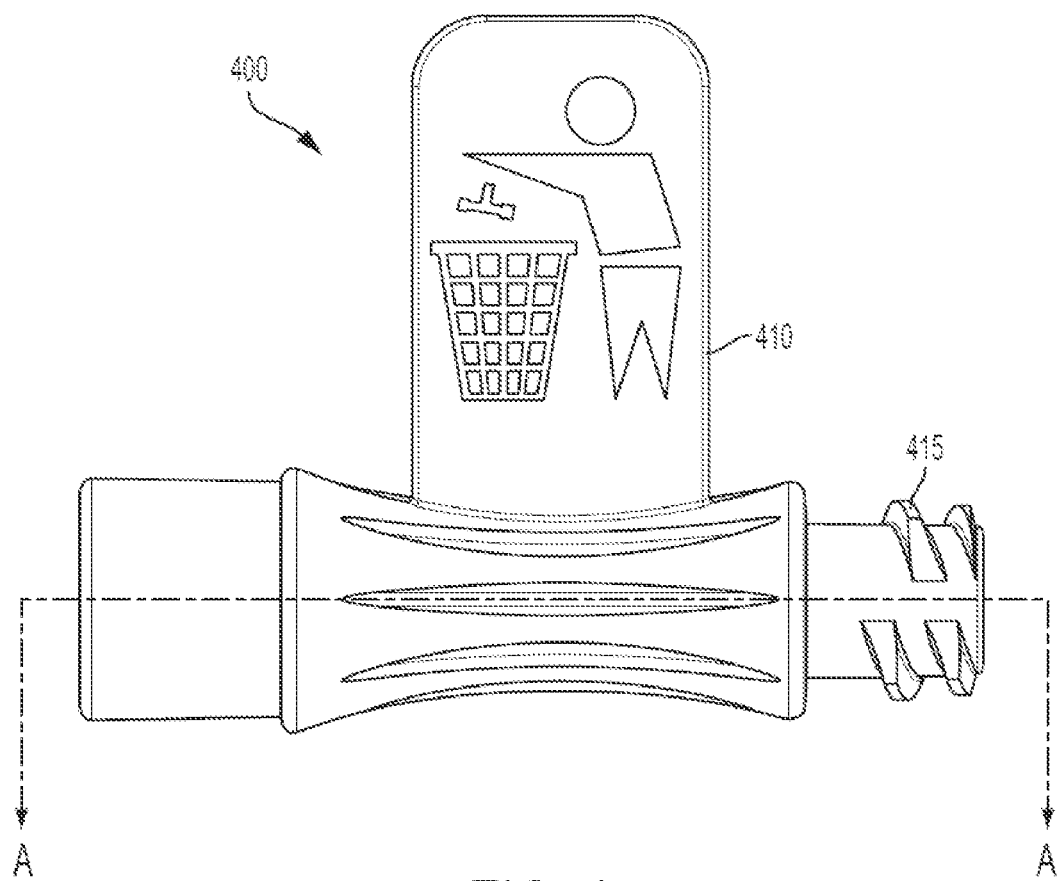
FIG. 4 is a side view of an interconnector, according to one or more embodiments of the disclosed subject matter.
Figure 5:
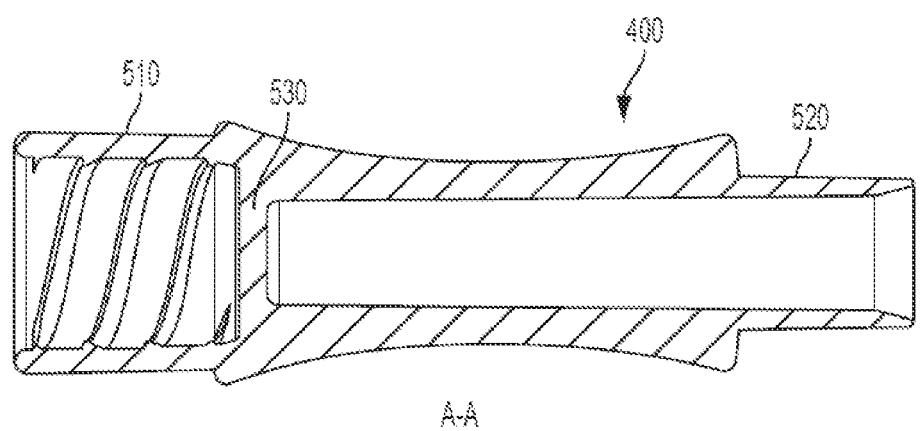
FIG. 5 is a longitudinal, cross-sectional view of the interconnector of FIG. 4, according to one or more embodiments of the disclosed subject matter.

The above-described embodiments use the Halkey Roberts valve 211 with male and female connectors 206, 207. Other types of self-sealing connectors are known and may be used as well. These make connection convenient because the connections are self valving and no pinch clamps are required. However, these connectors cannot be packaged and stored in the open position as the elastomer (typically silicone) valve parts can be permanently affected due to material creep. To facilitate the use as well as packaging and storage of the priming set, an interconnector 400 as seen in FIG. 4 and FIG. 5 may be employed. This interconnector 400 may be brightly colored, or otherwise configured to make conspicuous to the user the fact that it is removable. The interconnector 400 may be shaped to hold the male and female self-sealing connections together without activating or opening the valves. The interconnection may hold the self-sealing connectors in an inline arrangement such that their axes are collinear just as when they are connected, except that they are further apart. This interconnection arrangement is used during storage and shipping and mimics the interconnections that are made during use of the fluid circuit but without activating the automatic valves which would cause the elastomer that causes automatic closure to creep during storage. The distinguishing features such as colors and the tab 410 help the user to notice and remember to remove the interconnector prior to use. By packaging the components held together by the interconnector 400, it makes it easier for the user to recognize and establish the correct interconnections as well as prevent entanglement of tubing that could make interconnection more difficult. In addition, the therapy machine may display an appropriate software instruct the user how to use the priming set up, how to remove the inter connector, how to reconnect, perform the prime, and how to insert in the newly primed blood treatment device in series or replace and existing blood treatment device.

Figure 6:
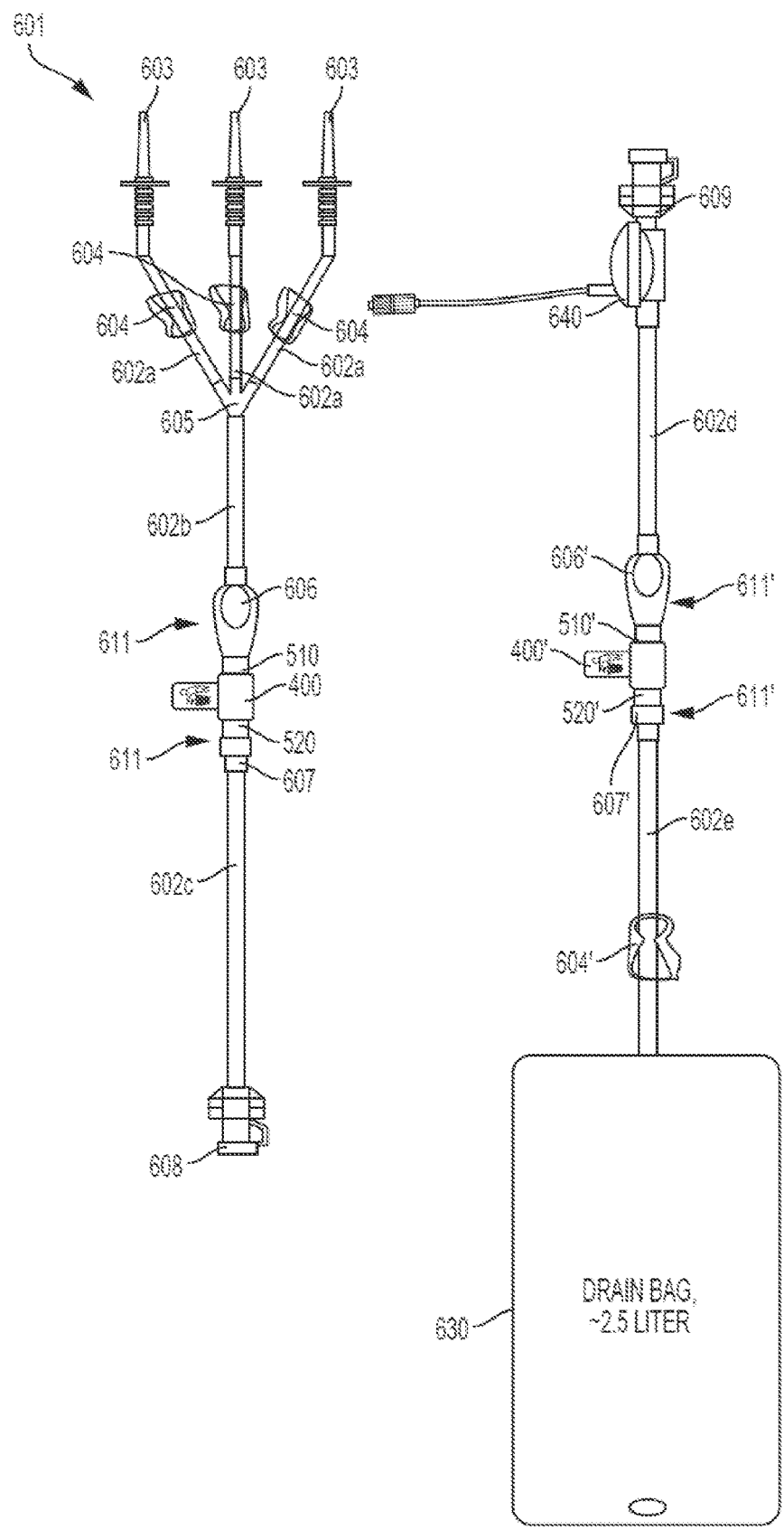
FIG. 6 is a drawing of a priming assembly with a pressure monitoring pod and three saline spikes, according to one or more embodiments of the disclosed subject matter.

FIG. 5 illustrates a cross section of the interconnector in FIG. 4. The section is taken through the plane indicated at A-A in FIG. 4. In this embodiment of the disclosed subject matter, the interconnector 400 is designed to not seal with standard luer connectors, but instead to act as a sterile barrier cap as well as holding the assembly together so the user knows how the assembly is to be configured for use. The interconnector is also configured to provide an interference fit with the mating connectors to help ensure they do not inadvertently fall off in shipping and storage. Specifically, the interconnector 400 includes a male connection end 510 that is configured to connect to the male connector half 206 of the self-sealing connector 211 and a female connection end 520 that is configured to connect to the female connector half 207 of a self-sealing connector 211, for example, a Halkey-Roberts valve 211. As seen in FIG. 5, an interior wall 530 extends across the diameter of the connector 400 and between the male connection end 510 the female connection end 520 and prevents any fluid communication between the male connector half 206 of the self-sealing connector 211 and the female connection end 520. In the embodiment of FIG. 6, for example, the interconnector ties the self-sealing connectors 611 and 611' together without permitting flow between them and without activating and distorting the elastomeric material used by the self-sealing connectors 611 and 611' (e.g., Halkey Roberts-type connectors) during storage of a fluid circuit. Such activation opens a self-sealing elastomeric seal by distorting it, which if maintained for a long time as in storage, would cause creep and could prevent it from re-sealing.

FIG. 6 is a drawing of a fluid circuit set that according to the method and devices described above. A packaged fluid circuit 601 may be provided in a sterile bag 650. The fluid circuit may contain components for use with the blood circuit for example, it may optionally include a pressure monitoring pod 640. A plurality of bag spikes 603 may be provided for accessing a source (e.g. bag) of saline. Self-sealing connector set 611 and 611' in the priming assembly 601 for perfusion blood treatment devices or sepsis filters (for example, for a 3 Spike version) as it would come out of the packaging separated by the interconnector 400, including the pressure monitor pod 640. Such blood treatment devices as illustrated in FIG. 6 may lack filtrate ports. For example, a sepsis filter may have microtubular fibers that are coated with binding agent and may be arranged such that no flow through the walls of the fibers occurs. In this embodiment of the blood treatment device priming set 601, there are multiple bag spikes 603, for example 3, each with a tube 602a with one each connected to an outlet end of one of the 3 bag spikes 603, and closeable by a respective pinch clamp 604. A diverging connector 605 with the 3 input ends connected to the 3 tubes 602a and the 1 output connected to an input end of a second length of tubing 602b that is in turn connected at an output end to a male part 606 of the self-sealing connector set 611. An opposite end of the male half 606 is connected to the male connection end 510 of the interconnector 400 and the female connection end 520 of the interconnector 400 is connected to the female half 607 of the self-sealing connector set 611. An output end of the female half 607 may be connected to an input end of a third length of tubing 602c and an output end of the third length of tubing 602c is connected to a DIN connector 608 (see ANSI/AAMI/ISO 8637-2010), which in this embodiment is color coded red to aid in the correct connection with the blood treatment device.

A second DIN connector 609 may be connected to an input end of the pressure measurement pod 640 and an output end of the pressure measurement pod 640 (which may be generally configured as described in US patent publication 20070179422 to Schnell or alternatives are similar devices such as inline pressure transducers) may be connected to an input end of a fourth length of tubing 602d. In this embodiment, the second DIN connector 609 may be color coded, for example the color blue, to aid in the correct connection with the blood treatment device which may be correspondingly color coded. An output end of the fourth length of tubing 602*d* is connected at an output end to a male half 606' of a second self-sealing connector set 611'. An opposite end of the male half 606' may be connected to the male connection end 510' of a second interconnector 400' and the female connection end 520' of the second interconnector 400' may be connected to the female half 607' of the self-sealing connector set 611'. An output end of the female half 607' may be connected to an input end of a fifth length of tubing 602*e* and an output end of the fifth length of tubing 602*e* may be connected to a drain bag 630 with a capacity of 2.5 liters, which is the priming volume of a blood treatment device (not shown), the priming volume of the blood treatment device priming set 601 and an amount to take into account variation in amount of saline and priming volumes. A fourth pinch clamp 604' may be attached around and configured to close the fifth length of tubing 602*e* just before the drain bag 630.

In a method according to one or more embodiments of the disclosed subject matter, saline bags (not shown in FIG. 6 but as illustrated elsewhere, for example at 710 or 210 in FIG. 2) that are connected to the saline spikes 603 are hung at a height above the blood treatment device (also not shown, but see 220 from FIG. 2), which in turn is mounted above the location of the drain bag 630, as illustrated schematically in FIG. 6. The vertical distance between the saline bags, the blood treatment device and the drain bag 630 can determine the speed at which the blood treatment device may be primed and flushed. By positioning the saline bags (not shown in FIG. 6 but as illustrated elsewhere, for example at 710) above the blood treatment device and the drain bag 630 below the saline bag or bags sufficient to produce a siphon effect, the blood treatment device is primed. The vertical distances can be optimized for the variety of blood treatment devices anticipated and allow for a prime within a predefined period of time. For example, the net fluid column can be adjusted to produce a desired pressure differential and concomitant flow rate by adjusting the relative elevations of saline bags and drain bag 630.

In the illustration of the multi spike example in FIG. 6, although not explicitly shown, the bag or bags of saline are hung and spiked so that the saline fills the tubing 602*a-c* up to the connection of the blood treatment device, fills the blood treatment device, then fills the drain line 602*d-e* after the blood treatment device. The saline flows via gravity through the blood treatment device and into the drain bag 630. The flow continues until the drain bag 630 has reached its capacity, then the flow stops automatically. A benefit of this technique is that the user performing the priming does not have to observe and halt the priming process in order to prevent air or other gas or gasses entering the blood treatment device. A further benefit is that the blood treatment device may be primed consistently by different workers using a predefined volume of saline. Note that other types of priming fluid may be used.

In embodiments, a tubing set for priming blood treatment devices may include self-sealing connectors that eliminate the need for pinch clamps by opening the fluid path upon connection and sealing fluid when disconnected either prior to or after priming. Such valves are available off the shelf, for example, but not limited to, Halkey-Roberts connectors 211, which have a male connector half 206 and a female connector half 207. As mentioned elsewhere, these self-sealing valves may employ an elastomer that is subject to creep which can undermine their ability to seal.

Figure 7:
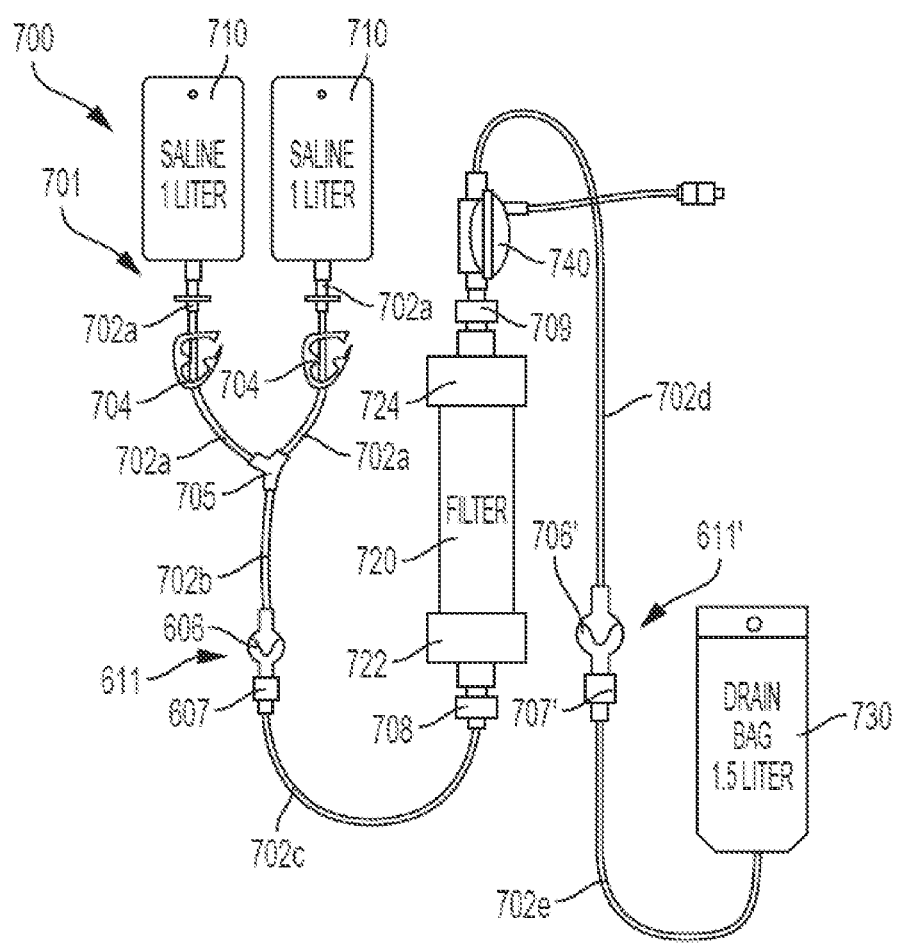
FIG. 7 is a drawing of a setup for priming using a priming assembly with a pressure monitoring pod similar to that of FIG. 6, except with just two saline spikes, according to one or more embodiments of the disclosed subject matter.

FIG. 7 is a drawing of a setup for priming 700 using a priming assembly 701 with a valve 711, a pressure measuring/monitoring pod 740 and a drain bag 730 similar to that of FIG. 6, having 2 saline spikes 703, according to one or more embodiments of the disclosed subject matter. FIG. 7 shows the priming assembly 701 (2 Spike version) with a pressure measuring/monitoring pod 740 after it is connected to a Sepsis filter 720 for the priming step.

In FIG. 7 a blood treatment device priming set 701, similar to blood treatment device priming set 600, has 2 bag spikes 703 that carry priming fluid through 2 tubes 702*a* with join at a Y-branch 705. Pinch clamps 704 may be attached at any point along the fluid circuit to halt flow and prevent leaking of fluid. Priming fluid flows through tubes 702*a* a length of tubing 702*b* that is in turn connected at the self-sealing connector 711. The self-sealing connector 711 includes mating male 706 and female 707 parts. The female part 707 is connected to a third length of tubing 702*c* which leads to a DIN connector 708, which may be color coded to aid in the correct connection with the blood treatment device 720. A second DIN connector 709 is connected to a pressure measurement pod 740 and in turn connected to a fourth length of tubing 702*d*. The second DIN connector 709 may also be color coded to aid in the correct connection with the blood treatment device 720. The fourth length of tubing 702*d* leads to a male part 706' of a second self-sealing connector 711'. A female part 707' of the self-sealing connector 711' is connected through line 702*e* to a drain bag 730. In embodiments, the drain bag 730 has a capacity of 1.5 liters, which is a selected priming and flushing volume of a blood treatment device (not shown), which may take into account the volume of the blood treatment device priming set 701 and a volume determined to desirable for flushing the blood treatment device of air or other gas or gasses and other materials, for example manufacturing residual materials.

In a method according to one or more embodiments of the disclosed subject matter, but with specific reference to the embodiment of FIG. 7, in the priming setup 700 multiple saline bags 710 are hung a height above the blood treatment device 720, which in turn is mounted above the drain bag 730, as illustrated schematically in FIG. 7. The vertical distance between the saline bags 710, the blood treatment device 720 and the drain bag 730 can determine the speed at which the blood treatment device is primed and flushed. As long as the saline bags 710 are above the blood treatment device 720 and the drain bag 730 is below the saline bag, the blood treatment device 720 will prime. The vertical distances can be optimized for the variety of blood treatment devices anticipated to be used and to allow for a prime of each type of blood treatment device within a predefined period of time.

In the illustration of the two bag spike example in FIG. 7, the two bags of saline 710 are hung and spiked so that the saline fills tubing 702*a*-702*c* that is connected to output ends of the bag spikes 703 up to a connection of the blood treatment device 708, fills the blood treatment device 720, fills the pressure measurement pod 740, then fills a drain line 702*d*, 702*e* after the pressure measurement pod 740. The saline flows via gravity through the drain lines 702*d*, 702*e*, the second valve 711' and into the drain bag 730. The flow continues until the drain bag 730 has reached its capacity, then the flow stops automatically due to the volume limitation of the drain bag 730. As above, the benefit of this technique is that the user performing the priming does not have to observe and halt the priming process in order to ensure that no air or other gas or gasses enters the blood treatment device 720. The flow can be stopped by engaging a pair of pinch clamps 704 that are connected around the tubing sections 702*a* connected to the bag spikes 703.

In embodiments, in addition to the gravity priming and automatic halting of the priming process, a tubing set for priming blood treatment devices can include self-sealing connectors 711, 711' that eliminate the need for pinch clamps by opening the fluid path upon connection and sealing fluid prior to connection or after disconnection. Such valves are available off the shelf, for example, but not limited to, Halkey-Roberts connectors 711, which have a male connector half 706, 706' and a female connector half 707, 707'.

Figure 8:
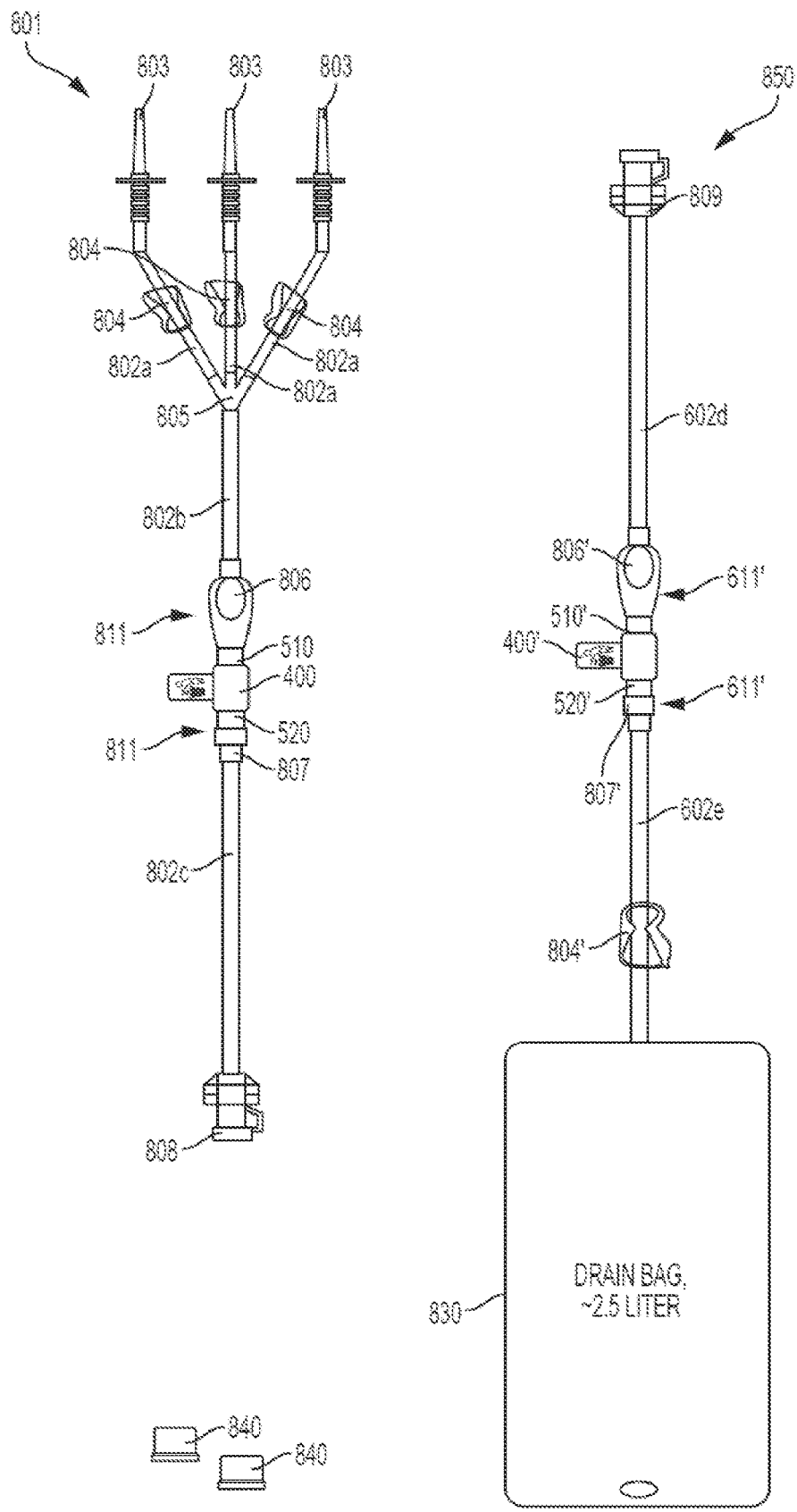
FIG. 8 is a drawing of a priming assembly with vented Hansen caps and three saline spikes, according to one or more embodiments of the disclosed subject matter.

FIG. 8 shows a priming assembly 801 in a sealed package 850 with vented Hansen caps 840. The Hansen caps may be of any type that can vent air or other gas or gasses from the non-blood side of a blood treatment device, preferably without loss of priming fluid. A description of the use of vented caps in priming as well as other details that may be employed in connection with the currently-disclosed subject matter is described in US Patent Publication 20150367062 to Brugger. The recommendations in this publication, such how to orient the blood treatment device, the flow direction during priming, etc. are applicable here as well. In FIG. 8, the circuit is generally the same as the embodiment of FIG. 6 except that it has no pressure pod 640 and does include the venting Hansen caps 840. Note that venting caps could also be included in the embodiment of FIG. 6 as well. The venting caps 840 allow for the priming of the dialysate portion of a dialyzer by venting air or other gas or gasses through the Hansen caps which are basically vented caps that block the flow of water, for example using a gas permeable hydrophobic membrane.

In the embodiment of the blood treatment device priming set 801 shown in FIG. 8, there are 3 bag spikes 803, 3 tubes 802a with one each connected to an outlet end of one of the 3 bag spikes 803, 3 pinch clamps 804 attached around each tube 802a are positioned to close the 3 tubes 802a, a 3 input and 1 output connector 805 with the 3 input end connected to distal ends of the 3 tubes 802a and the 1 output connected to an input end of a second length of tubing 802b that is in turn connected at an output end to a male half 806 of the self-sealing connector 811. An opposite end of the male half 806 is connected to the male connection end 510 of the interconnector 400 and the female connection end 520 of the interconnector 400 is connected to the female half 807 of the self-sealing connector 811. An output end of the female half 807 is connected to an input end of a third length of tubing 802c and an output end of the third length of tubing 802c is connected to a DIN connector 808, which in this embodiment is color coded red to aid in the correct connection with the blood treatment device.

A second DIN connector 809 is connected to an input end of a fourth length of tubing 802d, in this embodiment the second DIN connector 809 is color coded blue to aid in the correct connection with the blood treatment device. An output end of the fourth length of tubing 802d is connected at an output end to a male half 806' of a second self-sealing connector 811'. An opposite end of the male half 806' is connected to the male connection end 510' of a second interconnector 400' and the female connection end 520' of the second interconnector 400' is connected to the female half 807' of the self-sealing connector 811'. An output end of the female half 807' is connected to an input end of a fifth length of tubing 802e and an output end of the fifth length of tubing 802e is connected to a drain bag 830 with a capacity of 2.5 liters, which is the priming volume of a blood treatment device (not shown), the priming volume of the blood treatment device priming set 801 and an amount to take into account variation in amount of saline and priming volumes. A fourth pinch clamp 804' is attached around and configured to close the fifth length of tubing 802e just before the drain bag 830. The kit shown in FIG. 8 may be provided in a sealed bag 850 as a product of manufacture for priming predefined blood treatment devices to permit them to be swapped out during a treatment such as dialysis. The priming solution may be provided in the kit as well. The contents of the sealed bag 850 may be sterilized, for example by sterilizing the bag 850 and contents after sealing.

Figure 9:
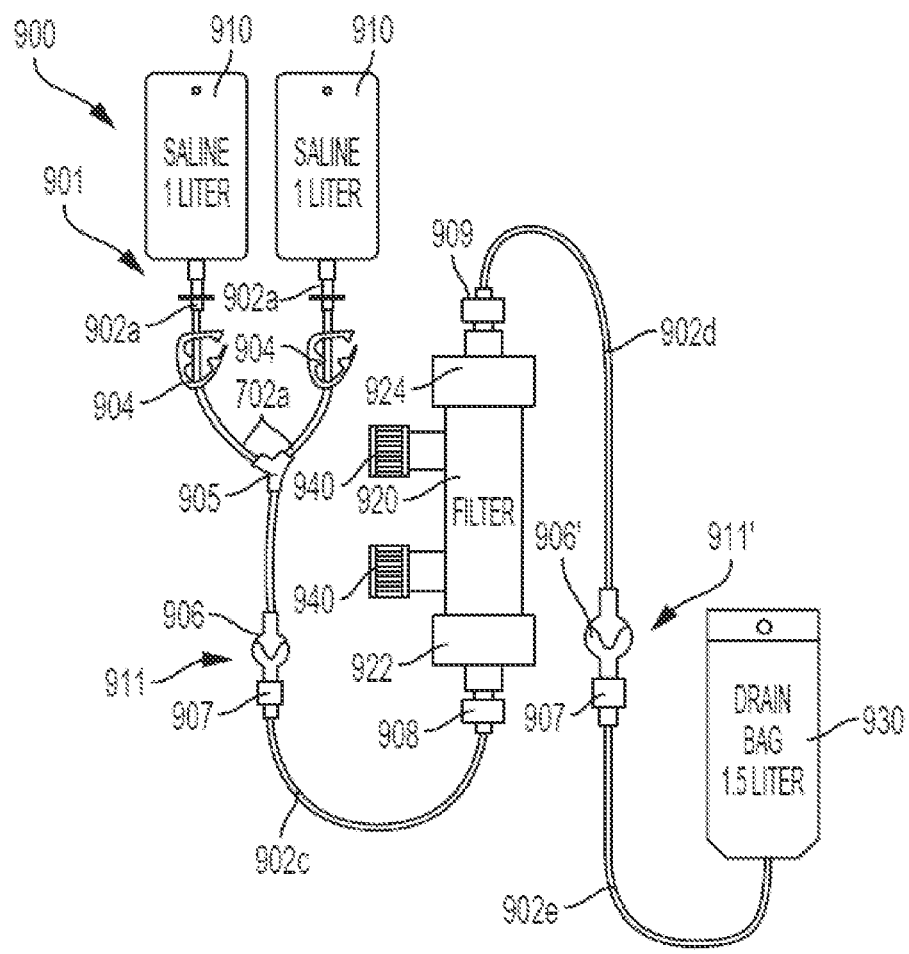
FIG. 9 is a drawing of a setup for priming using a priming assembly with vented Hansen caps and three saline spikes similar to that of FIG. 8, according to one or more embodiments of the disclosed subject matter.

FIG. 9 is a drawing of a fluid circuit for priming 900 using a priming assembly 901 with vented Hansen caps 840, but only 2 saline spikes 903 similar to that of FIG. 8, according to one or more embodiments of the disclosed subject matter. FIG. 9 shows the priming assembly 901 (2 Spike version, similar to FIGS. 1 and 7) after it is connected to a dialyzer blood treatment device for the priming step, but with vented Hansen Caps 840 being added.

As used throughout the specification, the term Hansen cap and Hansen connector can be replaced with any type of cap and connector suitable for the function discussed. Hansen connectors are commonly used in fluid conveyance devices and are common on microtubular blood treatment devices, but other types can also be used and the disclosed subject matter is not limited to the use of these examples of particular types of connectors, ports, or the caps therefore.

In the embodiment shown in FIG. 9 of the blood treatment device priming set 901, there are the 2 bag spikes 903, 2 tubes 902a with one each connected to an outlet end of one of the 2 bag spikes 903, 2 pinch clamps 904 attached one each around and configured to close the 2 tubes 902a, a 2 input and 1 output "Y" connector 905 with the 2 input end connected to distal ends of the 2 tubes 902a and the 1 output connected to an input end of a second length of tubing 902b that is in turn connected at an output end to the valve 911. The valve 911 includes a male half 906 and a female half 907. An output end of the female half 907 is connected to an input end of a third length of tubing 902c and an output end of the third length of tubing 902c is connected to a DIN connector 908, which in this embodiment is color coded red to aid in the correct connection with the blood treatment device 920. A second DIN connector 909 is connected to an input end of a fourth length of tubing 902d, in this embodiment the second DIN connector 909 is color coded blue to aid in the correct connection with the blood treatment device 920. An output end of the fourth length of tubing 902d is connected at an output end to a male half 906' of a second valve 911'. An opposite end of the male half 906' is connected to a female half 907' of the valve 911'. An output end of the female half 907' is connected to an input end of a fifth length of tubing 902e and an output end of the fifth length of tubing 902e is connected to a drain bag 930 with a capacity of 1.5 liters, which is the priming volume of a blood treatment device (not shown), the priming volume of the blood treatment device priming set 901 and an amount to take into account variation in amount of saline and priming volumes. A fourth pinch clamp 904' is attached around and configured to close the fifth length of tubing 902e just before the drain bag 930.

In a method according to one or more embodiments of the disclosed subject matter, but with specific reference to the embodiment of FIG. 9, in the priming setup 900 multiple saline bags 910 are hung a height above the blood treatment device 920, which in turn is mounted above the drain bag 930, as illustrated schematically in FIG. 9. The vertical distance between the saline bags 910, the blood treatment device 920 and the drain bag 930 can determine the speed at which the blood treatment device is primed and flushed. The saline bags 910 may be elevated above the blood treatment device 920 and the drain bag 930 below the saline bag, the blood treatment device 920 will prime. The vertical distances can be optimized for the variety of blood treatment devices anticipated to be used and to allow for a prime of each type of blood treatment device within a predefined period of time.

In the illustration of the two bag spike example in FIG. 9, the two bags of saline 910 are hung and spiked so that the saline fills tubing 902a-902c that is connected to output ends of the bag spikes 903 up to a connection of the blood treatment device 908, fills the blood treatment device 920, then fills a drain line 902d, 902e. The saline flows via gravity through the drain lines 902d, 902e, the second valve 911' and into the drain bag 930. The flow continues until the drain bag 930 has reached its capacity, then the flow stops automatically. Air or other gas or gasses flows from the dialyzer ports through the Hansen caps 940 as the blood treatment device 920 is flushed and primed but fluid does not leave the fluid compartment because of the hydrophobic membrane. In this way, air or other gas or gasses is completely purged. Because this is done in an unattended manner, the length of time for priming is less urgent (the attending user does not need to stand by while the priming proceeds). The flow can be halted by engaging a pair of pinch clamps 904 that are connected around the tubing sections 902a connected to the bag spikes 903.

In embodiments, in addition to the gravity priming and automatic stopping of the priming process, a tubing set for priming blood treatment devices can include the first and second valves 911, 911' that eliminate the need for pinch clamps by opening the fluid path upon connection and sealing fluid prior to connection or after disconnection. Such valves are available off the shelf, for example, but not limited to, Halkey-Roberts connectors 911, which have a male connector half 906, 906' and a female connector half 907, 907'.

Figure 10:
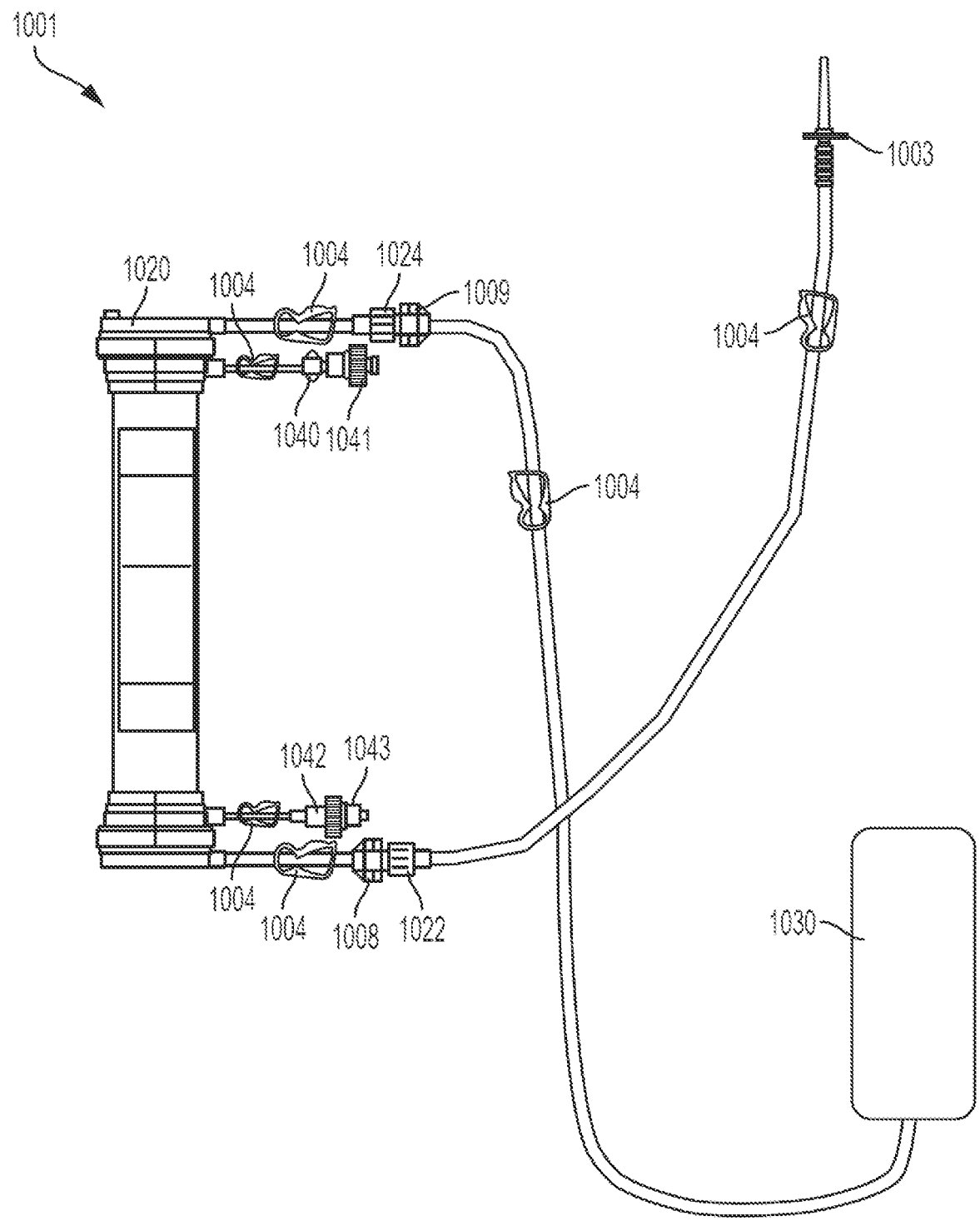
FIG. 10 is a drawing of a priming assembly with standard luer connections and pinch clamps and a single saline spike for use with a standard dialyzer, according to one or more embodiments of the disclosed subject matter.

FIG. 10 is a drawing of a priming assembly 1001 with standard luer connections 1040, 1041 and pinch clamps 1004 and a single saline spike 1003 for use with a standard dialyzer/blood treatment device 1020, according to one or more embodiments of the disclosed subject matter. In FIG. 10, a dialyzer configuration with the priming assembly 1001 as it would come out of the sterile packaging pre-attached to the blood treatment device 1020. Standard DIN Connectors 1008, 1009 and Luer Connectors 1040, 1042 are used, but in this configuration the Male connections point in the direction of fluid flow. Specifically, priming of the blood treatment device 1020 occurs through a first length of tubing 1002a that is connected to the saline spike 1003, through the female DIN connector 1008 and into the bottom of the blood treatment device 1020 and up to the top and out through the male DIN connector 1009 and into a second length of tubing 1002b and into a drain bag 1030. A female Luer 1040 is used at the dialysate entry and a male Luer 1042 is used at the dialysate exit, however, unlike with the priming, the flow of dialysate occurs through the top and then down through the body and the out the bottom of the blood treatment device 1020. In order to eliminate the possibility of incorrect connections, a female DIN connector 1009 is located at the entry for the blood path and a male DIN connector 1008 is located at the exit of the blood path. There is a general color coding that is used, Red for arterial (blood in), Blue for venous (blood out), Green for dialysate in, and Yellow for dialysate out. The vents 1041, 1043, in this case Transducer Protectors with micro porous membranes 1041, 1043, are used to allow the air or other gas or gasses out of the dialysate compartment, but keep the saline in. This allows the dialysate compartment to be filled passively and automatically. Halkey Roberts self-sealing connections and Interconnectors can also be used in a preattached dialyzer configuration, similar to the connections shown in FIG. 8.

As described above in relation to FIGS. 1-3, priming is from the bottom of the blood treatment device 1020 (or dialyzer) on the blood side. The saline fills the fibers, pushing any air or other gas or gasses up and out the top end of the blood treatment device into and then down a second length of tubing 1002b and into the drain bag 1030. For a dialyzer, the saline flows across the membrane into the dialysate chamber. Air or other gas or gasses from the dialysate chamber escapes out the vents on the dialysate ports (for example, Hansen ports) due to the vents used. The saline continues to flow until the drain bag is full, stopping the flow of saline. The drain bag is sized to have less volume than the combined volume of the saline bags, minus the fluid volume of the blood treatment device (or dialyzer). The flow of saline is stopped prior to emptying the saline bags so that no air or other gas or gasses is pulled into the freshly primed blood treatment device (or dialyzer).

Figure 11:
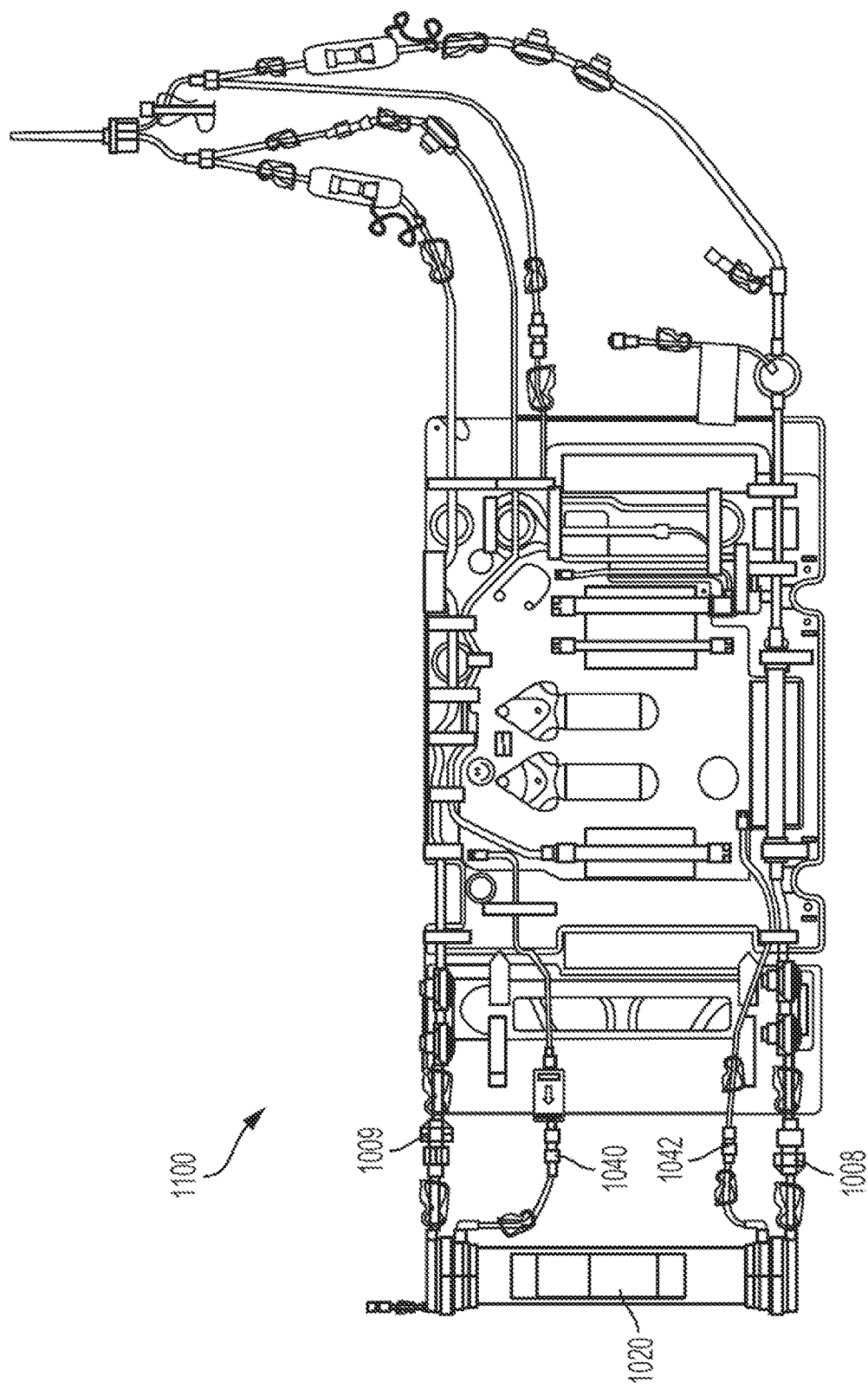
FIG. 11 is a drawing of a setup for priming using a priming assembly with standard luer connections and pinch clamps and a single saline spike similar to that of FIG. 10, according to one or more embodiments of the disclosed subject matter.

FIG. 11 is a drawing of a dialyzer system 1100 for use with the priming assembly 1001 with standard luer connections 1040, 1042, pinch clamps 1004 and a single saline spike 1003 similar to that of FIG. 10, according to one or more embodiments of the disclosed subject matter. FIG. 11 illustrates the blood treatment device cartridge 1020 embodiment with connector elements as would come out of the packaging and that would facilitate the use of the dialyzer 1020 with the priming assembly 1001 of FIG. 10. This is needed because sometimes during the course of a dialysis or hemofiltration therapy, the blood treatment device/dialyzer 1020 clogs or clots off Instead of discarding the whole disposable, a new dialyzer can be quickly primed and the clogged or clotted dialyzer can be quickly and efficiently changed out. Halkey Roberts self-sealing connections and Interconnectors can also be used in a configuration similar to FIG. 6.

Figure 12A:
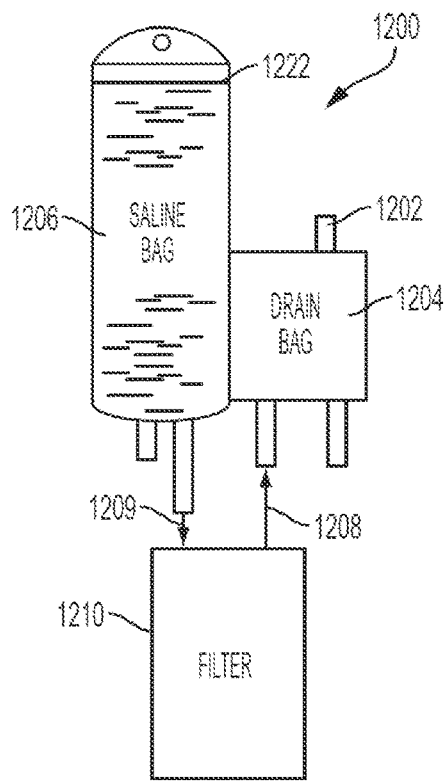
FIGS. 12A and 12B illustrate another method and optionally device embodiments for unattended priming of a blood treatment device.
Figure 12B:
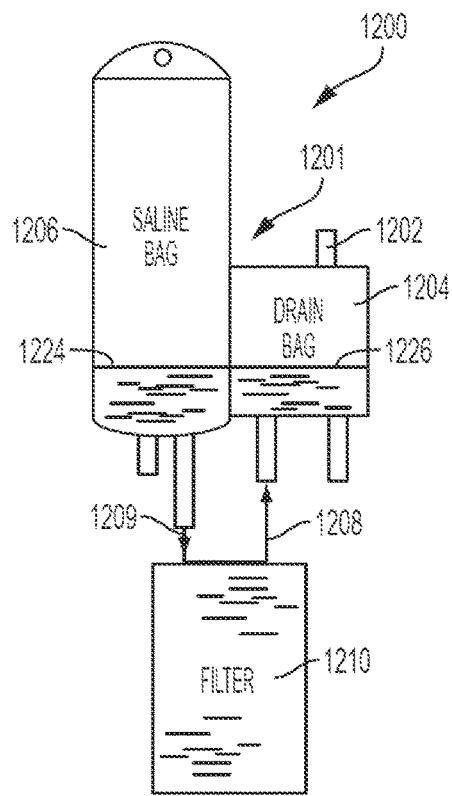

FIG. 12A shows a saline bag 1206 and a drain bag 1204 (which may be any type of containers) positioned at elevations such that as fluid drains from the saline bag 1206 into the drain bag 1204, the initially high fluid level 1222 of the saline in the saline bag 1206 drops to a same level as a level 1226 in the drain bag 1204 as shown in FIG. 12B. As indicated figuratively by arrows 1209 and 1208, fluid drains through a connected blood treatment device 1210 according to any of the features of the embodiments disclosed above. But rather than relying on the fixed volume drain bag to halt the flow of priming fluid, the fluid drains until the fluid columns stemming from the drain bag 1204 and saline bag 1206 reach equilibrium. A vent 1202 may be provided on the drain bag 1204. The vent 1202 may vent gas and prevent ingress of contaminants by isolating a sterile interior of the drain bag 1204 from the external environment using a sterile membrane (not shown). The sterile membrane may be hydrophobic to prevent egress of aqueous fluid from the drain bag 1204. A similar vent with a hydrophobic membrane may be used on a fluid line leading to the drain bag 1204 or on the blood treatment device body itself.

In embodiments, a saline bag 1206 may be pre-attached to a drain bag 1204 as a single article for use in priming. In other embodiments, a dual chamber bag may have one chamber full while the other chamber serves as the drain bag. The saline and drain bag dual chamber bags may be attached to each other as a single unit.

Figure 12C:
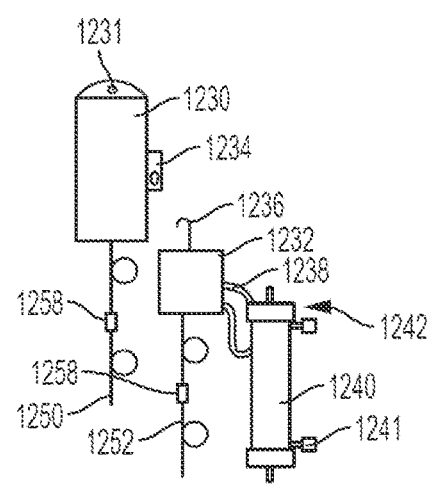
FIGS. 12C and 12D show alignment and positioning mechanisms for arranging a priming set-up that helps to ensure the alignment and positioning of the various components required according to embodiments of the disclosed subject matter.
Figure 12D:
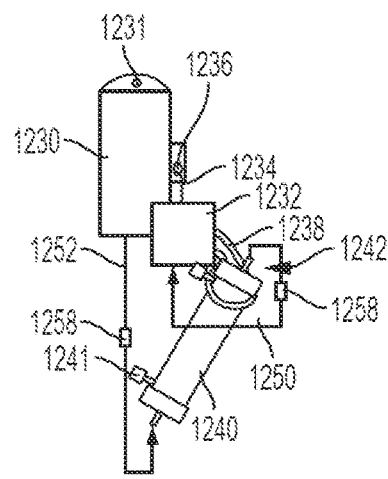

As shown in FIG. 12C, in further embodiments, the saline bag 1230 may have an attachment element 1234 such as a hook or hole to fit a complementary attachment element 1236 of the drain bag 1232 to allow the latter to be hung from the former. In still further embodiments, the drain bag 1232 may have an attachment mechanism 1238, such as a loop or strap to wrap around the blood treatment device 1240, to engage a feature 1242 of the blood treatment device 1240 (such as a ridge around a header chamber) to allow it to be, in turn, hung from the drain bag 1232. As shown in FIG. 12D, the interconnection of the saline and drain bags and the blood treatment device in this embodiment may ensure the correct levels of the bags and position and orientation of the blood treatment device (with vented caps 1241 in a desirable elevated position relative to the remainder of the blood treatment device 1240) to ensure that the fluid column primes the blood treatment device before reaching equilibrium and to ensure proper venting of air or other gas or gasses. Fluid circuits, with or without self-sealing connectors 1258 and with or without tubing clamps, as well as other features with respect to any of the various described embodiments are indicated figuratively at 1250 and 1252.

Figure 12E:
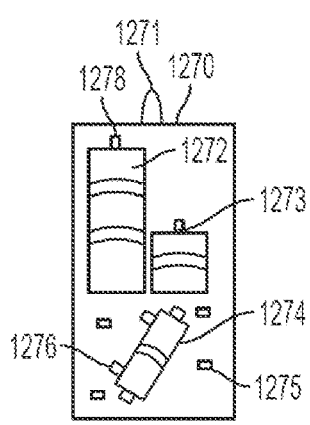
FIG. 12E shows further alignment and positioning mechanisms for arranging a priming set-up that helps to ensure the alignment and positioning of the various components required according to embodiments of the disclosed subject matter.
Figure 12F:
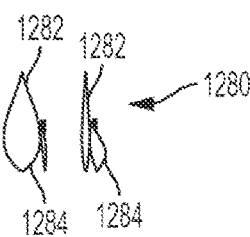
FIG. 12F illustrates a feature for variation of the embodiment of FIG. 12 E.

FIG. 12E shows a support 1270 with engagement elements 1272, 1273, and 1274 shaped and sized to receive a saline container, a drain container, and a blood treatment device (not shown in FIG. 12E). The support 1270 may be, for example, a thermoformed panel with cutouts at 1272, 1273, and 1274 shaped and sized to receive a saline container, a drain container, and a blood treatment device. Further features such as recesses or other types of features, indicated at 1276 and 1278 may be shaped to engage features of the saline container, a drain container, and/or blood treatment device shaped. For example, 1278 may be a hook to support the saline bag. For another example, 1276 may be a recess and clasp to hold dialyzer port protrusions from the blood treatment device so that the vented caps are arranged elevated relative to the blood treatment device when the blood treatment device is placed in the engagement element 1274. In an alternative embodiment, the support 1270 has an engagement element for a single double chamber bag 1280 as shown in FIG. 12F that includes saline bag 1282 and drain bag 1284 (with vent) as discussed above. The drain bag 1284 may be attached to the saline bag so that the double chamber bag 1280 is supported by the support 1270 thereby eliminating a separate engagement element 1273 for the drain bag.

The arrangement of FIG. 12D can be provided with the saline and drain bags preconnected (not the fluid lines, but inter-attached to form a unit as in FIG. 12D) so that the whole assembly can be hung from a hanging element 1231 such as a hole to hang on a hook of a support pole. The arrangement can include the blood treatment device, or not, depending on whether the blood treatment device is supplied as part of the packaged article of manufacture. The arrangement of FIG. 12E can also be provided with the saline and drain bags preconnected (again, not the fluid lines, but attached to the support 1270 as a unit as in FIG. 12E) so that the whole assembly can be hung from a hanging element 1271 such as a loop or hole (not shown) to hang on a hook of a support pole. The arrangement can include the blood treatment device, or not, depending on whether the blood treatment device is supplied as part of the packaged article of manufacture.

Figure 13:
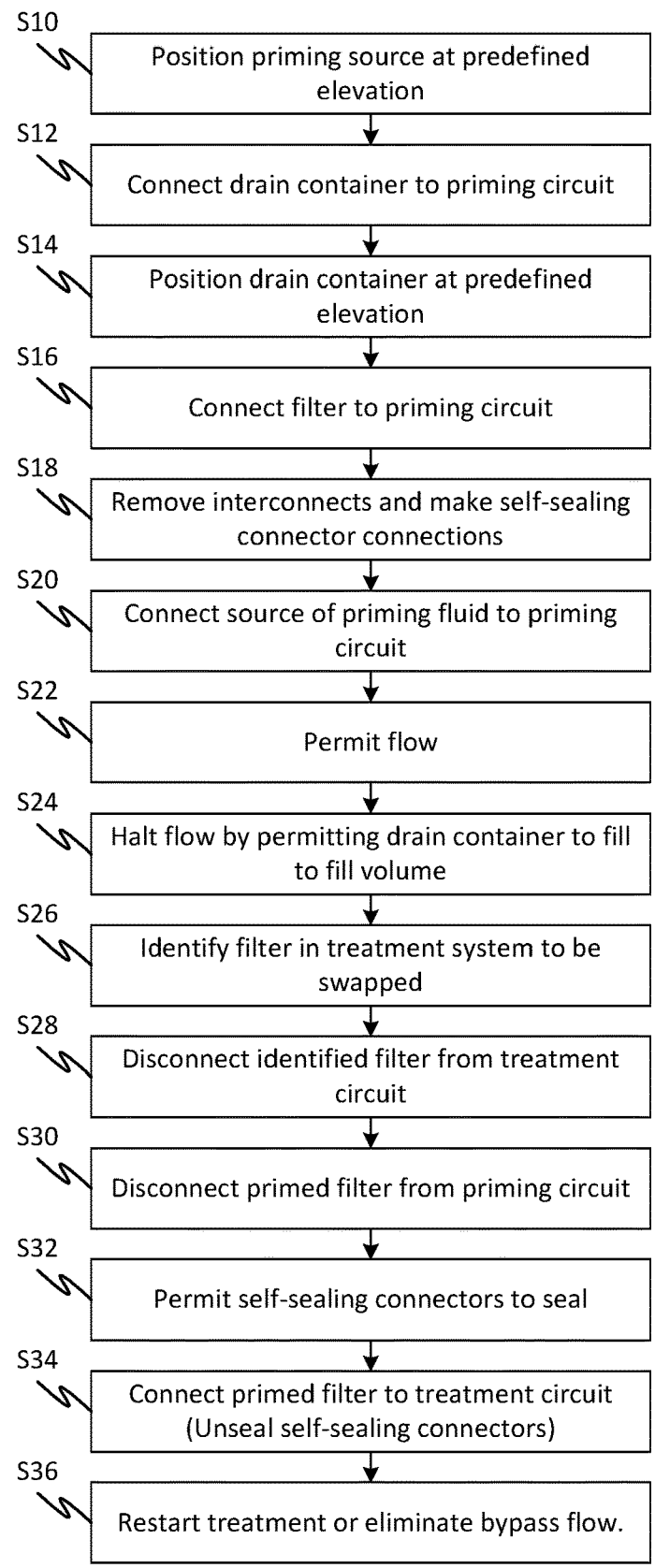
FIG. 13 is a method of priming and swapping a blood treatment device during a treatment, according to embodiments of the disclosed subject matter.

Referring to FIG. 13, a method of priming a treatment device is shown. The operations shown as S2 through S36 may be ordered differently and may be done in series, parallel, or combinations of series and parallel, according to alternative embodiments and operations may be omitted according to still further embodiments. These and the series method illustrated may also include swapping out a treatment device currently being used for a treatment and replacing it with one primed according to the method of priming, such as a blood treatment device, may begin with positioning a priming source at a particular elevation at S10. This may include hanging or positioning a container of priming fluid on a fixture (holder or support being equivalent terms) that ensures the priming fluid source is held at a particular elevation. The purpose is to ensure that priming fluid can siphon passively through a priming circuit that is positioned relative to this support and thereby ensure a flow of fluid. Alternative mechanisms for causing a flow include providing a fluid pump with a mechanism to ensure that the flow can be halted by the generation of a predefined head pressure. A pump with a maximum head pressure or a reverse check valve with a recirculation fluid line and cracking pressure may be employed, for example.

At S12, if not already preconnected, a drain container may be connected to a priming circuit. The priming circuit may be as simple as a tube with a blood treatment device connector at one end and a drain container connector at the other. The tube may have a tubing clamp preattached to the line. In other embodiments, there may be an intermediate connector that is continuous with the tube that allows the connections to be separated for swapping out a primed blood treatment device as discussed in embodiments herein. The tube intermediate connectors may be self-sealing connectors. As discussed above, the self-sealing connectors may be connected by interconnect members that are shaped to connected to the interconnect members but which interconnect members do not unseal the self-sealing connectors and thereby cause distortion of an elastic material therein.

A S14, the drain container may be positioned at predefined elevation. This, cooperatively with step S10 ensures that a flow can be established passively through the priming circuit. If an active flow device is employed, the elevation difference between the priming fluid source and the drain container may matter less or effectively not at all so steps S10 and S14 may not be limited to predefined elevations, strictly or at all. Also, the elevations at S10 and S14 may be relative to each other, the absolute positions being irrelevant, as will be understood by persons of skill in the art, the objective being to flow fluid from a source to a receiver (drain container). Note that equivalent mechanisms for halting flow are described with reference to FIG. 14 which may be used in alternative methods that do not employ a drain container but otherwise follow the current method operations.

At S16 a treatment device (blood treatment device, dialyzer, or any type of device as for all the embodiments) is connected to the priming circuit. The priming circuit may include the portion discussed with respect to S12 and also a portion to connect the priming fluid source. The latter may take the shape of any of the options discussed relative to the portion discussed with respect to S12 except that it may connect the blood treatment device to the priming fluid source. Either portion of the priming circuit may be preconnected to the source and drain containers and delivered that way or the priming circuit may have sealed connectors (to maintain sterility of a flow channel therein) for connection, respectively to the drain and source containers and the blood treatment device to be primed. Again, any time the term blood treatment device is used throughout the specification, it may be replaced by a term for any other device to be primed including any other type of blood treatment device or other treatment device.

The priming circuits that have interconnect members connecting their parts may be made continuous flow paths by removing the interconnect members and making the respective connection at S18. The main function of the interconnect members for the intermediate connections is to facilitate putting the priming circuit components together. If the self-sealing intermediate connectors were connected as delivered, to keep the independent parts count low in a delivered fluid circuit kit, the self-sealing connectors would suffer distortion of their internal sealing members, which generally being of elastomeric material, suffer creep when strained for an extended period such as during storage and shipment. As in all the embodiments, a function provided by having intermediate connections is that it provides fluid conveying segments for attachment to a treatment circuit when swapped in and for attachment to the priming circuit when primed. Effectively it may act as an adapter to permit interconnection between the circuits. In alternative embodiments, the intermediate connectors, including the self-sealing elements, can be integrated in a blood treatment device in which case the priming circuit may be simplified. In embodiments with intermediate connectors that are not self-sealing, the flow paths between the intermediate connectors and either side of the blood treatment device may be sealed using manual tube clamps.

At S20, the priming fluid source is connected to the priming fluid circuit to permit a flow into the blood treatment device. The elevations of the source and drain having been established to permit a siphon flow, the priming flow will continue S22 without attendance by the operator and halted by itself S24 without intervention. This allows an operator to set up a priming operation for a blood treatment device to be swapped in during a treatment without attending to the priming flow. The operator may thus establish the priming configuration and then direct attention to other matters such as additional patients or an on-going treatment operation. In alternative embodiment, particularly ones that do not employ natural siphoning but rather use an active pump, the drain may be any type of drain and the pump may flow a predefined volume, for example by counting rotations of a peristaltic rotor. Unattended priming may be provided by such means as well. However, the additional equipment required may be disadvantageous.

One of the functions provided by the unattended priming systems and methods disclosed herein is to permit the swapping (substitution; replacement) of a treatment device during an on-going treatment with minimal interruption of the treatment and with minimal diversion of attention by an operator. At S26, which may occur prior to any preparation for priming at all (i.e., prior to S20), a blood treatment is established and a need identified for the replacement of one or more blood treatment devices being used therein, including the blood treatment device connected to the priming circuit at S16. In this case, the treatment may involve the use of multiple blood treatment devices and the method may be done sequentially or contemporaneously to prime multiple blood treatment devices for a single treatment. The need for replacement of a blood treatment device may manifest as an adverse rise in pressure, an indication of a leak in a membrane, an indication of expiration of a blood treatment device or a prediction thereof based on volume of fluid processed, another evident failure or fouling of a blood treatment device or any other indication, including a prediction of a need for replacement or even a risk that blood treatment device may, will, or has ceased functioning in a predefined manner.

Once one or more blood treatment devices has been identified for replacement, the treatment may be halted or the blood treatment device bypassed, depending on the type of treatment and system, and the blood treatment device to be replaced may be disconnected out of the treatment system at S28. The blood treatment device that has been primed, after at least a time sufficient to allow full priming at S22, may be disconnected from the priming circuit at S30. At S32, in embodiments, the disconnection of the blood treatment device from the priming circuit is effective to seal self-sealing connectors connected to the primed blood treatment device. In other embodiments, tube clamps are clamped instead and the intermediate connectors disconnected. At S34, the primed blood treatment device is connected to the treatment system which unseals self-sealing connectors if present. Otherwise tubing clamps are released. The treatment is then restarted or the bypass of the now-replaced blood treatment device is eliminated at S36. The blood treatment devices swapped in and out by the foregoing method or any of the other disclosed methods may be identical such that the type of treatment performed is not modified by the swapping of the blood treatment device. In this and any methods, the blood treatment devices may be of any type including hemofilters, dialyzers, apheresis blood treatment devices, adsorbent blood treatment devices, and other types of treatment devices. Blood treatment devices may be of the type known as microtubular fiber blood treatment devices commonly used in dialysis.

Figure 14:
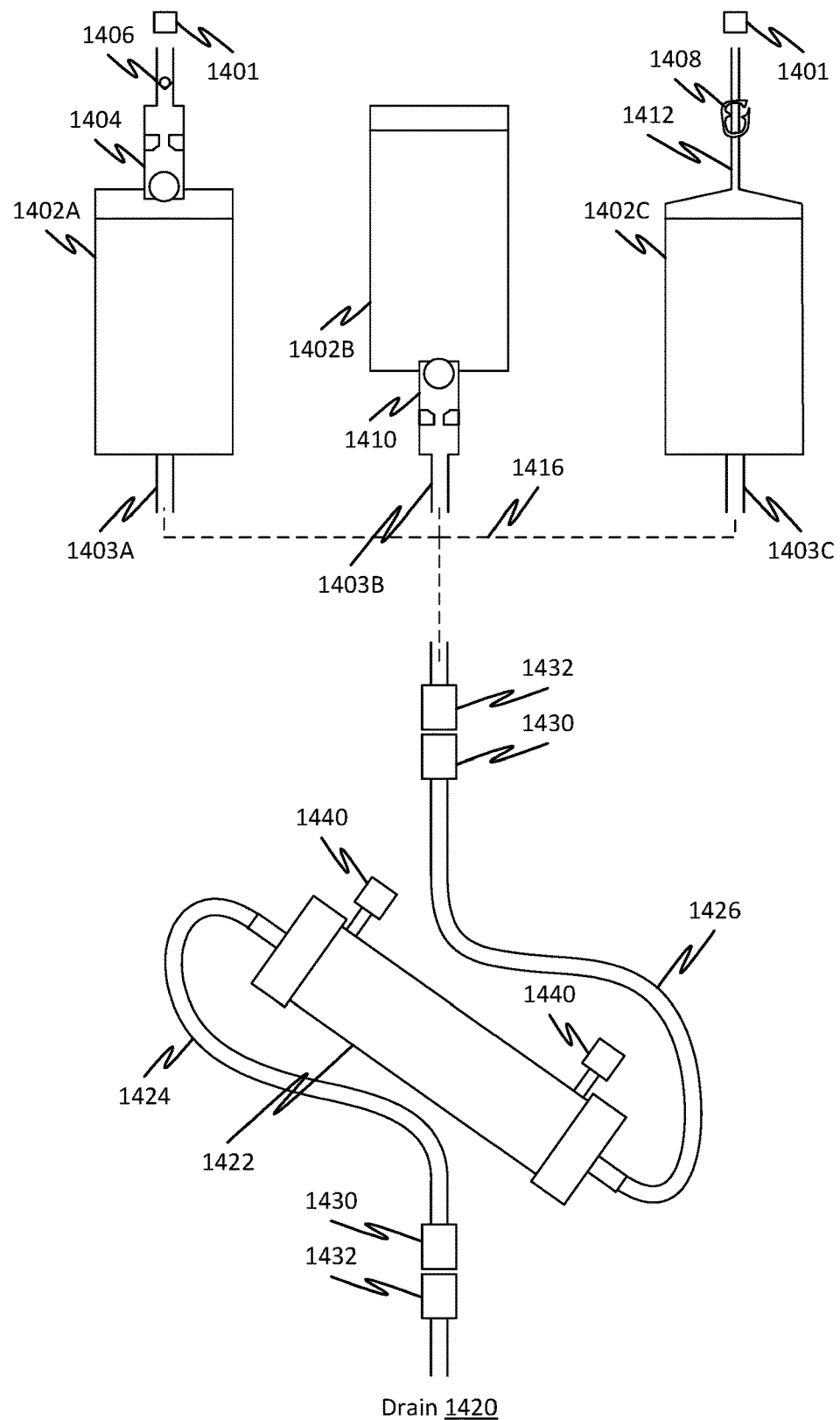
FIG. 14 is a drawing that represents multiple priming circuit embodiments in which the siphon flow of fluid is starved by preventing flow from the source side of the circuit rather than the filling of a drain container.

FIG. 14 shows priming circuit embodiments in which priming fluid flow may be halted by the generation of a negative pressure in the source of fluid rather than by relying on the prevention of flow after the filling of a fixed volume drain bag. In the present embodiments, priming fluid is supplied through a respective container 1402A-1402C. Container 1402A has a float valve a1404 and a check valve 1406 that allows air or other gas or gasses to be released from the container, for example by squeezing it, and prevent incursion of air or other gas or gasses back into the container a1402A. The float valve 1404 allows fluid to be pushed up to a level that closes the float valve 1404 and the prevention of incursion of air or other gas or gasses back through the check valve prevents the fluid level from falling again. The container 1402A can have a loop or other engagement mechanism to permit it to be hung in a preferred orientation to ensure the proper operation of the float valve 1404. The tube 1403A leads to a connector 1432 as indicated by the dashed line 1416 which shows the three alternative continuous flow paths for the three alternative container 1402A-1402C embodiments.

The connector 1432 connects to the remainder of a priming circuit including portions that connect to a blood treatment device 1422. The remainder of the priming circuit may be as in any of the embodiments. For example, the connector pair 1432 and 1430 may be self-sealing connectors. Or there may be a tube clamp (not shown in the present drawing but shown elsewhere) on line 1426 to allow it to be manually sealed if the connectors 1430 and 1432 are not self-sealing. Line 1424 may lead to a drain 1420 which may be a collection container, collection bag, or a permanent drain fixture or bucket. Since the flow of priming fluid in the present embodiments is halted by starving the suction side, the fixed volume drain container is not required.

In this and other embodiments, a cap 1401 or other type of seal may be provided to ensure against the leakage of fluid from the container 1402A-1402C. The flow path 1416 also indicates here that the container outlet 1403A leads to connector 1432. The connector 1432 connects to the rest of a priming circuit which includes the other features of the priming circuit discussed with regard to the other embodiments, namely, first and second intermediate connectors 1432/1430 blood treatment device 1422 with vent caps 1440 and respective lines 1426 and 1424. It should be evident from the flow path of the tubes 1424 and 1426 that the priming circuit may be set up to siphon except that in this case, the flow may be halted by the ebbing of flow from the source side of the circuit as a result of the starvation of the source and the prevention of a flow of air or other gas or gasses into the priming circuit. Thus, in such embodiments, there is no need for another flow limiter as in other embodiments, such as a drain container, to halt the flow. However, the other flow limiter embodiments may be combined with the source starvation embodiments of the embodiments of FIG. 14 to form further embodiments.

Container 1402B has a float valve 1410 in a reverse orientation that permits a flow of priming fluid from the container 1402B but blocks a flow of air or other gas or gasses through the float valve 1410. The float valve 1410 also leads to connector 1432. In use, this embodiment allows a priming fluid container that contains air or other gas or gasses to be positioned to generate a siphon and the float valve 1410 halts the flow of priming fluid before air or other gas or gasses passes through the float valve 1410. Here again, the dashed line 1416 indicates that an outlet 1403B is connected to the connector 1432 by a continuous length of tubing as is the outlet 1403A. A third container 1402C has an air or other gas or gasses purge tube 1412 with a manual tubing pinch clamp 1408 that allows air or other gas or gasses to be purged from the container 1402C, for example by squeezing it. After air or other gas or gasses is fully purged, the manual tubing pinch clamp 1408 can be closed and fluid from the container 1402C may flow by siphon effect to prime the blood treatment device until the container 1402C is starved, whereupon flow halts without any air or other gas or gasses getting into the priming circuit, at least as far as the blood treatment device 1422. Here again, the dashed line 1416 indicates that an outlet 1403B is connected to the connector 1432 by a continuous length of tubing as is the outlet 1403C. Effectively but providing the float valves in the in containers 1402A and 1402B, the flow of priming fluid is also starved by the closure of the valve, in the case of 1402A resulting in the starvation of the flow from the container 1402A itself and in the case of the container 1402B, by starvation of the flow from the outlet of the container 1402B. Note that a float valve or an equivalent may be placed at a different point in the priming circuit such as along tubes 1426 to provide a similar effect of preventing air or other gas or gasses from entering the blood treatment device. Alternatives to the float valves could be a fully saturated membrane which can prevent the flow of air or other gas or gasses through it by high surface tension forces.

In the embodiments of FIG. 14, the vents connected to the non-blood side may include check valves to prevent air from being sucked into the blood treatment device.

Figures 15A, 15B:
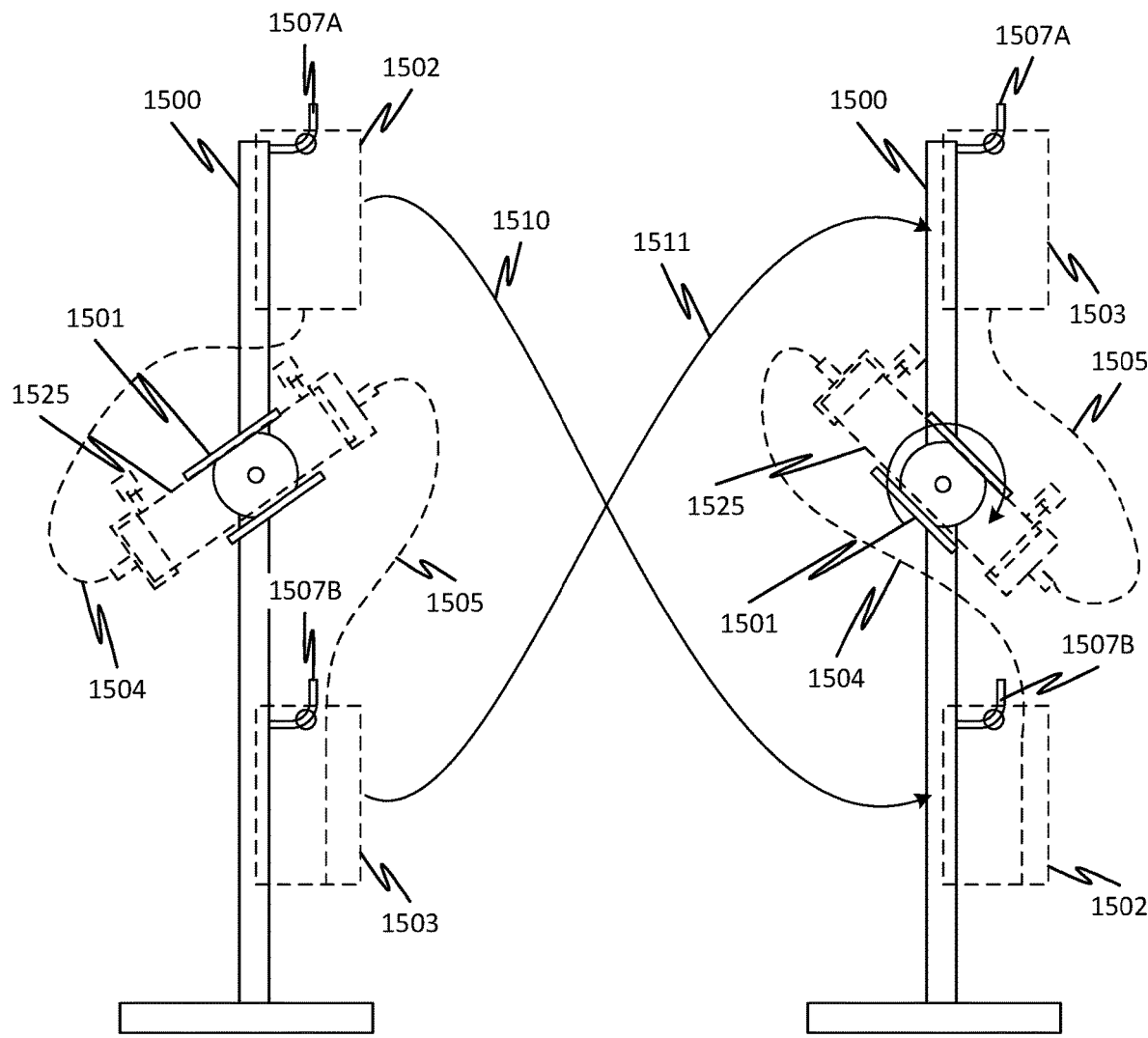
FIGS. 15A through 15C are for illustrating a priming method and also to show a priming fixture configured to implement the method, according to embodiments of the disclosed subject matter.
Figure 15C:
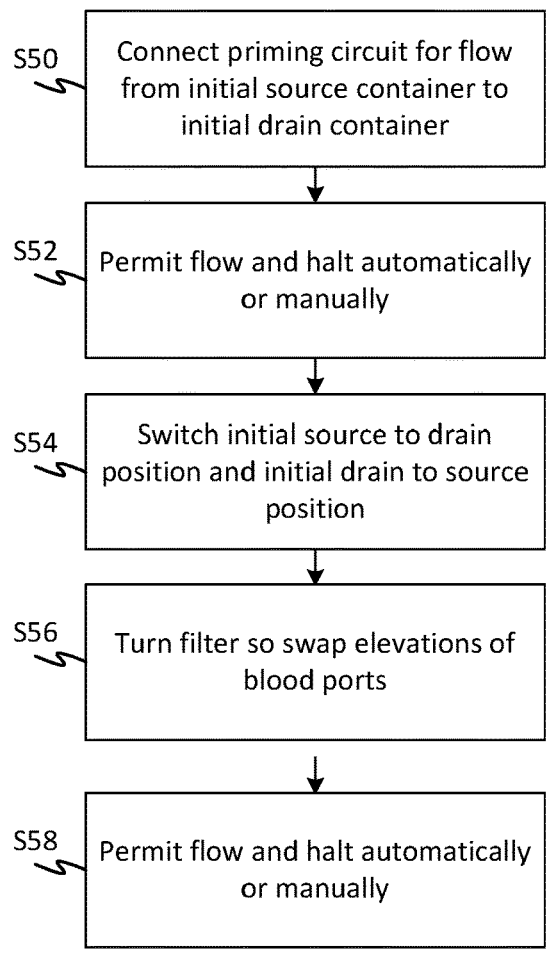

Referring now to FIGS. 15A, 15B, and 15C, a priming method shown in FIG. 15C is for priming in a first direction through a blood treatment device and then switching the direction and orientation of the blood treatment priming in the opposite direction. Again, the blood circuit of the blood treatment device is being primed and all the incidents of the other embodiments may be applied here as well to form additional embodiments. The new teaching here introduced is the changing of priming direction. This has been found to help to eliminate suborn bubbles in certain types of blood treatment devices, for example, microtubular fiber blood treatment devices such as used in dialysis. The method includes connecting a priming circuit to a blood treatment device and initial source and drain containers at S50. S50 also includes positioning the initial source and drain containers at appropriate elevations to cause a flow from a lower blood port on the blood treatment device to a higher blood port on the blood treatment device so that the priming flow is in an upward direction. Then at S52, the flow is permitted to proceed, such as by gravity, until it halted, either manually or automatically as described with reference to the embodiments. That is, for example, by starving the supply or over-filling (pressurizing) the drain container. At S54, after priming in a first direction, the blood treatment device is pivoted so that the relative elevations of the blood ports are switched and the priming fluid source and drain containers are switched. The at S56, the priming flow proceeds again as before in the opposite direction until at S58 the flow is halted by some means as described herein or otherwise. FIGS. 15A and 15B show a mechanism for implementing the method of FIG. 15C. A support 1500 which may take the form of an intravenous pole with upper 1507A and midlevel 1507B hooks. A pivoting support 1501 holds a blood treatment device 1525 shown in dashed liens and has two endpoint positions that allow the vented filtrate side ports to expel air or other gas or gasses as the blood treatment device 1525 is primed. The pivoting support may permit a user easily to tilt the blood treatment device 1525 for flow in the opposite directions described with reference to the method of FIG. 15C. The source and drain containers 1502 and 1503, respectively, can conveniently take swapped positions by changing the hooks 1507A and 507B on which they are hung. The priming circuit lines 1504 and 1505 may be of any form including those described herein, such as ones with a pair of self-sealing connectors. The lines 1510 and 1511 illustrate the swapping of the positions of the initial source 1502 and initial drain 1503 containers. Note that the method of claim 15C may include multiple cycles of flow-direction-switching.

Figure 16A:
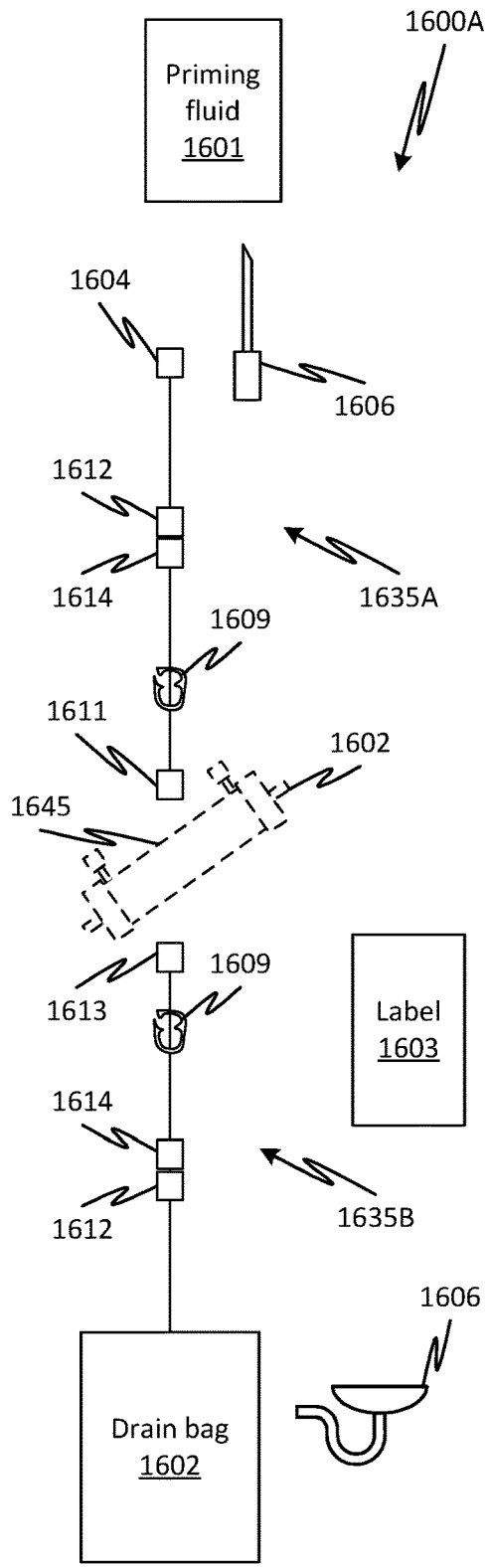
FIGS. 16A and 16B illustrate various embodiments of a priming circuit and treatment circuit according to embodiments of the disclosed subject matter.
Figure 16B:
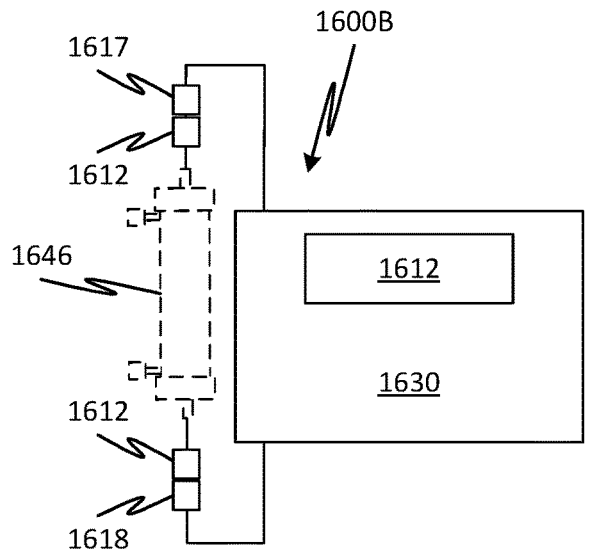

FIG. 16A shows a priming circuit 1600A which may take the form of any of the disclosed embodiments therefore. FIG. 16B shows a treatment circuit which also may take the form of any of the disclosed embodiments. The priming circuit 1600A has source 1635A and drain 1635B lines which may be continuous or interconnected by respective sets of connectors 1612 and 1614. As described clamps 1609 may be provided or the connectors 1612 and 1614 may be self-sealing. The source line 1635A may have a connector 1604 such as a male luer which may be connectable to a bag spike 1606 or the connector 1604 may be connectable to a predefined source container 1601. The source line 1635A may alternatively be pre-attached, integrally or by connector, to the bag spike 1606. A drain container 1602 may be pre-attached or a connector for a collection container may be connected to the drain line 1635B. Alternatively, the drain line 1635B may have a termination for use with a drain or bucket 1606. When a blood treatment device 1645 is primed, the connectors 1612 and 1614 pairs can be disconnected from the rest of the priming circuit and connected to connectors 1617 and 1618 of the treatment circuit 1600B after removal of a blood treatment device 1646 currently used in the treatment circuit 1600B. The connectors 1617 and 1618 may be self-sealing connectors as in any of the other embodiments. The connectors 1617 and 1618 may be non-self-sealing connectors as in any of the other embodiments. The treatment circuit 1600B may be used with any suitable treatment machine 1630. The treatment machine 1630 may have a display 1612 on which it is programmed to display instructions for performing any of the methods described in the claims or otherwise described in the instant specification. The priming circuit 1600A and any components thereof may be packaged with printed instructions 1603 for performing any of the methods described in the claims or otherwise described in the instant specification.

Any of the methods described herein may be incorporated in, or embodied in, instructions for use of a priming kit. Instructions for priming a blood treatment device may include instructions for performing one or more of the following operations.

Orienting a blood treatment device having first and second blood ports connected by a blood flow path running through the blood treatment device such that the first blood port is below the second blood port, connecting a source of priming fluid to the first blood port, connecting a drain to the second blood port, causing the source of priming fluid generates a pressure sufficient to force priming fluid from the first blood port to the second blood, stopping the flow of priming fluid before any air or other gas or gasses enters the first blood port, disconnecting the blood treatment device without letting any priming fluid escape, and connecting the blood treatment device to a blood treatment circuit.

Interrupting a blood treatment using the blood treatment circuit prior to connecting the blood treatment device to the blood treatment circuit and continuing the blood treatment thereafter.

The disconnecting may be effective automatically to seal off the blood path of the blood treatment device when the blood treatment device is disconnected.

The source of priming fluid may be caused to generate a pressure sufficient to force priming fluid from the first blood port to the second by elevating a container of priming fluid above the second port to cause a flow of priming fluid through the treatment device by gravity.

Before priming the blood treatment device, determine that a blood treatment device being used for the blood treatment needs to be replaced by the one to be primed and then proceeding to prime the one to be primed.

Disconnect the primed blood treatment device by undoing self-sealing connectors and connect the self-sealing connectors to the blood treatment circuit.

Disconnect the primed blood treatment device by clamping adapter lines connected to the primed blood treatment device and disconnecting the adapter lines from a remainder of the priming circuit thereby retaining the priming fluid in the adapter lines and blood treatment device and connecting the adapter lines to the blood treatment circuit.

The connecting the first blood port to a source of priming fluid and the connecting the second blood port to a drain includes a directive to connect a priming circuit with DIN connectors.

The connecting the first blood port to a source of priming fluid and the connecting the second blood port to a drain includes a directive to connect a priming circuit with a first tube having a DIN connector and a male luer or bag spike for connection to a bag of priming fluid and a second tube with a DIN connector and a connector for attachment to a collection bag.

The connecting the first blood port to a source of priming fluid and the connecting the second blood port to a drain includes a directive to connect a priming circuit with a first tube having a DIN connector and a male luer or bag spike for connection to a bag of priming fluid and a second tube with a DIN connector and a connector for attachment to a collection bag of inelastic film, two-layer film such that the collection bag has a predefined volume, a bag of stretchable film sized to fit a rigid container such as a bucket or other enclosure to ensure it can't expand when overfilled.

The collection bag may be preattached or the directions may include a directive to attach the collection bag to the second tube.

The tube may be divided by an interconnector that connects connectable self-sealing connectors in such a way that their internal elastomeric seal elements are not strained by the connection.

Disconnect the interconnector and connect the self-sealing connectors of the first and second tubes prior to priming the blood treatment device.

Note that in any of the embodiments, the priming fluid container may also be a rigid container. The container is sized such that the combination of the compressed trapped air or other gas or gasses and the fluid in the container stops the flow. Or, the rigid container could have an air or other gas or gasses vent that allows the container to fill completely with fluid, functioning similarly to an empty flat bag.

In any of the foregoing method embodiments, a treatment machine that engages a blood treatment device to be replaced may have a controller programmed to provide instructions to an operator for implementing any of the disclosed methods. A therapy machine with a monitor, user interface and software that facilitates the swapping of blood treatment devices or the addition of blood treatment devices, and a disposable bloodline/fluid line assembly with extra connections that facilitates the connection of a replacement blood treatment device and/or the addition of specialty blood treatment devices as prescribed by the physician. Monitor and software give prompts and feedback to the user about how and when to prime and connect blood treatment devices to the bloodline/fluid line assembly. The therapy machine specifically allows and facilitates swapping and/or addition of blood treatment devices, as well the bloodline/fluid line assembly has appropriate connectors to facilitate swapping and/or addition of blood treatment devices.

In one or more first embodiments, a tubing set can comprise a bag spike, a first tube, and a second tube. The bag spike is adapted for connecting to a predefined type of medical fluid bag. The medical fluid bag can be of a type having a predefined volume of fluid. The first tube is connected to the bag spike at an inlet end. An outlet end of the first tube has a first blood treatment device connector adapted for connection to a predefined blood treatment device at a first blood port thereof. The second tube has a second blood treatment device connector adapted for connection to the predefined blood treatment device at a second blood port thereof. The second tube can be connected to a bag (e.g., a drain bag) whose elastic properties and size are selected to ensure that the predefined volume of fluid held by the predefined type of medical fluid bag connectable by the bag spike is substantially more than blood and non-blood compartments volume of the predefined blood treatment device plus the volume of the drain bag.

In the first embodiments or any other embodiment, the drain bag is of nylon or other sufficiently strong sheet materials.

In the first embodiments or any other embodiment, the drain bag is of inelastic film.

In the first embodiments or any other embodiment, the predefined blood treatment device has self-sealing connectors that close and stop flow when disconnected.

In one or more second embodiments, a blood treatment device priming set can comprise a drain bag, a bag spike, and first and second tubes. The bag spike can be constructed to connect to a medical fluid bag having a predefined volume of fluid. The first tube has inlet and outlet ends. The first tube can be constructed to connect to the bag spike at the inlet end. The outlet end has a first blood treatment device connector constructed to connect to a first blood port of a blood treatment device. The second tube can be connected to the drain bag. The second tube has a second blood treatment device connector constructed to connect to a second blood port of the blood treatment device. The drain bag has elastic properties and a volume selected to ensure that the predefined volume of fluid held by the medical fluid bag is more than a volume of blood and non-blood compartments of the blood treatment device plus a volume of the drain bag.

In the second embodiments or any other embodiment, the drain bag includes at least one layer of nylon or is of nylon.

In the second embodiments or any other embodiment, the drain bag is of inelastic film.

In the second embodiments or any other embodiment, the predefined blood treatment device has self-sealing connectors that close and stop flow when disconnected.

In one or more third embodiments, a method of priming comprises connecting the set of any of the first and second embodiments, or any other embodiment, to the blood treatment device and permitting fluid to flow by gravity therethrough from the medical fluid bag to the drain bag. The method can further include permitting fluid to flow until the fluid is stopped by the attainment of a maximum capacity of the drain bag.

In the third embodiments or any other embodiment, the method can further comprise, when a currently-in-use blood treatment device being used in a blood treatment needs to be replaced, disconnecting said set from said blood treatment device and replacing said currently-in-use blood treatment device with said blood treatment device immediately thereafter.

In one or more fourth embodiments, a tubing set can comprise multiple bag spikes, and multiple tubes. Each bag spike is adapted for connecting to a predefined type of medical fluid bag. The medical fluid bag can be of a type having a predefined volume of fluid. Each one of the multiple tubes is connected to a separate one of the multiple bag spikes at an inlet end. An outlet end of each of the multiple tubes is connected to a multi-way connector to combine the contents of each of the multiple tubes into a single first tube that has a first blood treatment device connector adapted for connection to a predefined blood treatment device at a first blood port thereof. The first tube has a first connector with a first portion and a second portion positioned between the multi-way connector and the first blood treatment device connector with a first interconnector positioned between and connected to the first portion and the second portion. A second tube has a second blood treatment device connector at one end adapted for connection to the predefined blood treatment device at a second blood port thereof. The second tube at an opposite end is adapted for connection to a bag (e.g., a drain bag) whose elastic properties and size are selected to ensure that the predefined volume of fluid held by the predefined type of medical fluid bag connectable by the bag spike is substantially more than blood and non-blood compartments volume of the predefined blood treatment device plus the volume of the drain bag. The second tube has a second connector with a first portion and a second portion positioned between the second blood treatment device connector and the second tube opposite end with a second interconnector positioned between and connected to the first portion and the second portion. A pressure measurement pod is connected to the second tube adjacent to the second blood treatment device connector.

In the fourth embodiments or any other embodiment, the drain bag is of nylon.

In the fourth embodiments or any other embodiment, the drain bag is of inelastic film.

In the fourth embodiments or any other embodiment, the predefined blood treatment device has self-sealing connectors that close and stop flow when disconnected.

In the fourth embodiments or any other embodiment, the first and second interconnectors do not permit flow.

In one or more fifth embodiments, a blood treatment device priming set can comprise a drain bag, multiple bag spikes, and multiple tubes. Each bag spike is adapted for connecting to a predefined type of medical fluid bag. The medical fluid bag can be of a type having a predefined volume of fluid. Each one of the multiple tubes is connected to a separate one of the multiple bag spikes at an inlet end. An outlet end of each of the multiple tubes is connected to a multi-way connector to combine the contents of each of the multiple tubes into a single first tube that has a first blood treatment device connector adapted for connection to a predefined blood treatment device at a first blood port thereof. The first tube has a first connector with a first portion and a second portion positioned between the multi-way connector and the first blood treatment device connector. A second tube has a second blood treatment device connector at one end adapted for connection to the predefined blood treatment device at a second blood port thereof. The second tube at an opposite end can be connected to a bag (e.g., a drain bag) whose elastic properties and size are selected to ensure that the predefined volume of fluid held by the predefined type of medical fluid bag connectable by the bag spike is substantially more than blood and non-blood compartments volume of the predefined blood treatment device plus the volume of the drain bag. The second tube has a second connector with a first portion and a second portion positioned between the second blood treatment device connector and the second tube opposite end. A pressure measurement pod is connected to the second tube adjacent to the second blood treatment device connector.

In the fifth embodiments or any other embodiment, the drain bag is of nylon.

In the fifth embodiments or any other embodiment, the drain bag is of inelastic film.

In the fifth embodiments or any other embodiment, the predefined blood treatment device has self-sealing connectors that close and stop flow when disconnected.

In one or more sixth embodiments, a tubing set can comprise multiple bag spikes, and multiple tubes. Each bag spike is adapted for connecting to a predefined type of medical fluid bag. The medical fluid bag can be of a type having a predefined volume of fluid. Each one of the multiple tubes is connected to a separate one of the multiple bag spikes at an inlet end. An outlet end of each of the multiple tubes is connected to a multi-way connector to combine the contents of each of the multiple tubes into a single first tube that has a first blood treatment device connector adapted for connection to a predefined blood treatment device at a first blood port thereof. The first tube has a first connector with a first portion and a second portion positioned between the multi-way connector and the first blood treatment device connector with a first interconnector positioned between and connected to the first portion and the second portion. A second tube has a second blood treatment device connector at one end adapted for connection to the predefined blood treatment device at a second blood port thereof. The second tube at an opposite end is adapted for connection to a bag (e.g., a drain bag) whose elastic properties and size are selected to ensure that the predefined volume of fluid held by the predefined type of medical fluid bag connectable by the bag spike is substantially more than blood and non-blood compartments volume of the predefined blood treatment device plus the volume of the drain bag. The second tube has a second connector with a first portion and a second portion positioned between the second blood treatment device connector and the second tube opposite end with a second interconnector positioned between and connected to the first portion and the second portion. A pair of vented Hansen caps for connecting to the blood treatment device can also be included.

In the sixth embodiments or any other embodiment, the drain bag is of nylon.

In the sixth embodiments or any other embodiment, the drain bag is of inelastic film.

In the sixth embodiments or any other embodiment, the predefined blood treatment device has self-sealing connectors that close and stop flow when disconnected.

In the sixth embodiments or any other embodiment, the first and second interconnectors do not permit flow.

In one or more seventh embodiments, a blood treatment device priming set can comprise a drain bag, multiple bag spikes, and multiple tubes. Each bag spike is adapted for connecting to a predefined type of medical fluid bag. The medical fluid bag can be of a type having a predefined volume of fluid. Each one of the multiple tubes is connected to a separate one of the multiple bag spikes at an inlet end. An outlet end of each of the multiple tubes is connected to a multi-way connector to combine the contents of each of the multiple tubes into a single first tube that has a first blood treatment device connector adapted for connection to a predefined blood treatment device at a first blood port thereof. The first tube has a first connector with a first portion and a second portion positioned between the multi-way connector and the first blood treatment device connector with a first interconnector positioned between and connected to the first portion and the second portion. A second tube has a second blood treatment device connector at one end adapted for connection to the predefined blood treatment device at a second blood port thereof. The second tube at an opposite end can be connected to a bag (e.g., a drain bag) whose elastic properties and size are selected to ensure that the predefined volume of fluid held by the predefined type of medical fluid bag connectable by the bag spike is substantially more than blood and non-blood compartments volume of the predefined blood treatment device plus the volume of the drain bag. The second tube has a second connector with a first portion and a second portion positioned between the second blood treatment device connector and the second tube opposite end with a second interconnector positioned between and connected to the first portion and the second portion. A pair of vented Hansen caps for connecting to the blood treatment device can also be included.

In the seventh embodiments or any other embodiment, the drain bag is of nylon.

In the seventh embodiments or any other embodiment, the drain bag is of inelastic film.

In the seventh embodiments or any other embodiment, the predefined blood treatment device has self-sealing connectors that close and stop flow when disconnected.

In one or more eighth embodiments, a tubing set can comprise a bag spike, a first tube, and a second tube. The bag spike is adapted for connecting to a predefined type of medical fluid bag. The medical fluid bag can be of a type having a predefined volume of fluid. The first tube is connected to the bag spike at an inlet end. An outlet end of the first tube has a first blood treatment device connector adapted for connection to a predefined blood treatment device at a first dialysate port thereof. The second tube has a second blood treatment device connector adapted for connection to the predefined blood treatment device at a second dialysate port thereof. The second tube at an opposite end is adapted for connection to a bag (e.g., a drain bag) whose elastic properties and size are selected to ensure that the predefined volume of fluid held by the predefined type of medical fluid bag connectable by the bag spike is substantially more than blood and non-blood compartments volume of the predefined blood treatment device plus the volume of the drain bag.

In the eighth embodiments or any other embodiment, the drain bag is of nylon.

In the eighth embodiments or any other embodiment, the drain bag is of inelastic film.

In the eighth embodiments or any other embodiment, the predefined blood treatment device has self-sealing connectors that close and stop flow when disconnected.

In one or more ninth embodiments, a blood treatment device priming set can comprise a drain bag, a bag spike, a first tube, and a second tube. The bag spike is adapted for connecting to a predefined type of medical fluid bag. The medical fluid bag can be of a type having a predefined volume of fluid. The first tube is connected to the bag spike at an inlet end. An outlet end of the first tube has a first blood treatment device connector adapted for connection to a predefined blood treatment device at a first dialysate port thereof. The second tube has a second blood treatment device connector adapted for connection to the predefined blood treatment device at a second dialysate port thereof. The second tube can be connected to a bag (e.g., a drain bag) whose elastic properties and size are selected to ensure that the predefined volume of fluid held by the predefined type of medical fluid bag connectable by the bag spike is substantially more than blood and non-blood compartments volume of the predefined blood treatment device plus the volume of the drain bag.

In the ninth embodiments or any other embodiment, the drain bag is of nylon.

In the ninth embodiments or any other embodiment, the drain bag is of inelastic film.

In the ninth embodiments or any other embodiment, the predefined blood treatment device has self-sealing connectors that close and stop flow when disconnected.

In one or more tenth embodiments, a method of treatment includes connecting a plurality of bag spikes to separate medical fluid bags with each bag having a predefined volume of fluid and a first tube being connected to the plurality of bag spikes at an inlet end and connecting an outlet end of the first tube having a first blood treatment device connector adapted for connection to a predefined blood treatment device at a first blood port thereof. The method can also include connecting a second tube having a second blood treatment device connector adapted for connection to the predefined blood treatment device and a pressure measurement pod adjacent and distal to the second blood treatment device connector at a second blood port thereof with an outlet end of the second tube being connected to a drain bag; filling the blood treatment device with fluid from the medical fluid bags to prime the blood treatment device; and disconnecting the primed blood treatment device from the first tube and the second tube. The method can still further include disconnecting a used blood treatment device from a dialysis system; and connecting the primed blood treatment device to the dialysis system.

In one or more eleventh embodiments, a method of treatment includes connecting a plurality of bag spikes to separate medical fluid bags at an inlet end and connecting an outlet end of the first tube having a first blood treatment device connector adapted for connection to a predefined blood treatment device at a first blood port thereof. The method can also include connecting a second tube having a second blood treatment device connector adapted for connection to the predefined blood treatment device at a second blood port thereof with an outlet end of the second tube being connected to a drain bag; filling the blood treatment device with fluid from the medical fluid bags to prime the blood treatment device; and disconnecting the primed blood treatment device from the first tube and the second tube. The method can still further include disconnecting a used blood treatment device from a dialysis system; and connecting the primed blood treatment device to the dialysis system.

In one or more twelfth embodiment, a method for performing a blood treatment, includes flowing blood from a patient through an extracorporeal blood treatment system that uses a replaceable blood treatment device. The method includes detecting a condition indicating a need to replace the replaceable blood treatment device. The method includes priming a blood treatment device to provide a primed blood treatment device and replacing the replaceable blood treatment device with the primed blood treatment device.

According to variations thereof, in the one or more twelfth embodiments, the detecting includes detecting a change in a pressure of a blood circuit. According to variations thereof, in the one or more twelfth embodiments, the detecting includes detecting a pressure property indicating a rise in pressure drop through the replaceable blood treatment device. According to variations thereof, in the one or more twelfth embodiments, the flowing includes performing an extracorporeal blood treatment. According to variations thereof, in the one or more twelfth embodiments, the flowing includes performing a hemodialysis, hemofiltration, apheresis, or a type of renal replacement therapy treatment. According to variations thereof, in the one or more twelfth embodiments, the priming includes creating a siphon flow in a priming circuit and automatically halting the siphoning flow prior to an entry of air or other gas or gasses into the fluid circuit. According to variations thereof, in the one or more twelfth embodiments, the automatically halting includes the passive starvation of a flow from a priming source. According to variations thereof, in the one or more twelfth embodiments, the automatically halting includes the complete filling of a fluid-receiving device until it can hold no further fluid. According to variations thereof, in the one or more twelfth embodiments, the receiving device includes a drain bag of inelastic material. According to variations thereof, in the one or more twelfth embodiments, the receiving device includes a drain bag of relatively inelastic and relatively elastic materials bonded as a dual layer film. According to variations thereof, in the one or more twelfth embodiments, the receiving device includes a drain container with a maximum fill volume that is less than a total volume of fluid of a source container less a volume of the primed blood treatment device less a volume of a priming circuit between the primed blood treatment device and the drain container. According to variations thereof, in the one or more twelfth embodiments, the replacing includes disconnecting the primed blood treatment device from a priming circuit using self-sealing connectors. According to variations thereof, in the one or more twelfth embodiments, the self-sealing connectors remain connected to the primed blood treatment device after said disconnecting by means of lengths of tubing. According to variations thereof, in the one or more twelfth embodiments, the replacing includes clamping fluid lines attached to the primed blood treatment device prior to disconnecting the primed blood treatment device from a priming circuit and keeping the clamped fluid lines attached to the blood treatment device. According to variations thereof, in the one or more twelfth embodiments, the replacing includes connecting the clamped fluid lines to a blood circuit. According to variations thereof, in the one or more twelfth embodiments, the drain container is a bilayer bag that includes a layer of nylon. According to variations thereof, in the one or more twelfth embodiments, the drain container is a bilayer bag that includes two layers of film, a first a layer of the two layers of film being stiffer than a second of the two layers of film. According to variations thereof, in the one or more twelfth embodiments, the priming includes creating a siphon flow in a priming circuit and automatically halting the siphoning flow prior to an entry of air or other gas or gasses into the fluid circuit, wherein the automatically halting includes the passive starvation of a flow from a priming source by means of a valve that blocks the passage of air or other gas or gasses from a priming source but permits flow of priming fluid. According to variations thereof, in the one or more twelfth embodiments, the valve includes a float valve. According to variations thereof, in the one or more twelfth embodiments, the valve includes a wetted membrane. According to variations thereof, in the one or more twelfth embodiments, the automatically halting includes the complete filling of a fluid-receiving device until it can hold no more to prevent air or other gas or gasses from entering the primed blood treatment device. According to variations thereof, in the one or more twelfth embodiments, the automatically halting includes the complete filling of a fluid-receiving device until it can hold no more while maintaining a column of fluid to a level above the primed blood treatment device. According to variations thereof, in the one or more twelfth embodiments, priming includes providing a priming circuit with two lines connectable to blood ports of the primed blood treatment device, each line including two interconnected line portions. According to variations thereof, in the one or more twelfth embodiments, the to line portions are interconnected by self-sealing connectors, portions of which are connectable to a blood circuit to permit said replacing. According to variations thereof, in the one or more twelfth embodiments, the priming includes disconnecting an interconnector member from each of said self-sealing connector portions and connecting said self-sealing connector portions to interconnect said two line interconnected portions to form continuous flow paths in said two lines. According to variations thereof, in the one or more twelfth embodiments, the interconnector member connects respective ones of said connector portions in such a way that seals thereof are in an unstrained state. According to variations thereof, in the one or more twelfth embodiments, the seals thereof are elastomeric material subject to creep upon being strained.

In any of the method, device, or system embodiments that include or employ an interconnect member the interconnect member may be shaped to provide a sterile barrier between lumens of two predefined connectors forming an interconnectable pair. The sterile barrier may include a tortuous path between the lumens and an external environment.

Any of the embodiments that are described as including or employing a blood treatment device, including the embodiments defined by the claims, it will be understood that such embodiments may be modified to form an additional embodiment in which the blood treatment device is replaced with any type of blood treatment device or any type of conditioning element that requires priming.

In any of the embodiments, including those defined by the claims, a connector that connects to a blood treatment device may limited to one that conforms to American National Standards Institute (ANSI)/Association for the Advancement of Medical Instrumentation (AAMI)/International Organization for Standardization (ISO) for the connection of blood ports of a cardiovascular implant, extracorporeal system, hemodialyzer, hemodiablood treatment device, hemofilter or hemoconcentrator. In any of the embodiments, such a connector may be limited to one that conforms to ANSI/AAMI/ISO 8637:2010.

Although blood treatment devices that process blood are specifically disclosed herein, it is further contemplated that the systems, methods, and devices described herein can be applied to any types of fluid blood treatment devices including, for example, blood treatment devices that processes a bodily fluid other than blood. Accordingly, embodiments of the disclosed subject matter are not limited to a particular class of blood treatment devices.

Furthermore, the foregoing descriptions apply, in some cases, to examples generated in a laboratory, but these examples can be extended to production techniques. For example, where quantities and techniques apply to the laboratory examples, they should not be understood as limiting. In addition, although specific chemicals and materials have been disclosed herein, other chemicals and materials may also be employed according to one or more contemplated embodiments.

In this application, unless specifically stated otherwise, the use of the singular includes the plural and the use of "or" means "and/or." Furthermore, use of the terms "including" or "having," as well as other forms, such as "includes," "included," "has," or "had" is not limiting. Any range described herein will be understood to include the endpoints and all values between the endpoints.

In any of the embodiments, the blood treatment devices employed may be of any type including adsorbent based blood treatment devices such as hemoperfusion blood treatment devices, liver replacement blood treatment devices, microtubular fiber blood treatment devices, electrodialysis blood treatment devices, hemofilters, dialyzers, oxygenators, or any other type of blood treatment device or any other therapy device that allows the blood to flow through, especially those used in extracorporeal blood treatments.

In any of the method embodiments including a blood treatment, the method may include the performance of the blood treatment without anticoagulant or the use of anticoagulant at a reduced level. In the modified method, rather than rely on anticoagulant such as citrate or heparin to prevent to minimize clotting, the blood treatment device circuit, where the risk of clotting is greatest, typically occurs, is monitored for some indication of clogging. This may be may be predicted, progressive, actual, or inchoate clogging. Indicators of clogging may be a trend in pressure loss through the blood side of the blood treatment device, observation of the color of the blood treatment device, or some other indication. The user then determines to swap out the clogging blood treatment device or is prompted to by the therapy machine software and user interface. By simply swapping out the clogged blood treatment device with a fresh blood treatment device and preserving the bloodline and fluid set assembly, time and costs are saved.

Any of the self-sealing valves may be of the Halkey-Roberts type in various arrangements such as, for example, described in European Patent Publication EP1632264 to Halkey-Roberts Corporation. The details are not explained in the instant application because these types of connectors are known in the art and well-understood by those of skill in the art. But for purposes of convenience, in an example embodiment, a valve activation element shaped as a male luer pushes on an elastomeric valve sealing element changing its shape so as to open a passage in the male connector. In the embodiment, a female luer is covered by an elastomeric cover that is opened in piercing fashion by the male luer-shaped valve activation element of the other connector. Both elastomeric elements restore to a rest position that seals the openings of the respective connector. If either is maintained in an open state, come degree of yield or creep may occur preventing the rest position from sealing completely. A kit of the priming assembly is packaged and sterilized for the convenience of the user. The kit also contains instructions for performing the prime.

Note that in any of the embodiments or in the claims, the connectors for the blood treatment devices may be limited to the ISO standard mentioned here or to some other standard. Also, in any embodiment, a priming flow path through the blood treatment device may be open for the expulsion of gas or air or other gas or gasses. Also, at any point in the instant application or claims where air or other gas or gasses is identified, it will be appreciated that the disclosed subject matter is not limited to circumstances involving air or other gas or gasses and other gases may be involved such that the disclosure and claims may be read as indicating any type of gas.

Note that in any of the embodiments, the blood compartment of a blood treatment device may form a continuous circuit with the priming circuit between a source of priming fluid and a drain. The flow is halted by the drain. However, in any and all embodiments, the blood treatment device may have a porous media separating the blood compartment from a non-blood compartment such that in embodiments where vents are attached to the non-blood compartment, since the blood path is effectively open to the non-blood path due to the porous media, the continuous path is open to the outside. However, by selection of a hydrophobic vent, the circuit between the source of priming fluid and the drain can be closed. In embodiments where the choking of flow from the source side is used to halt the flow, the vents can include check valves to prevent air from being sucked into the blood treatment device during priming.++

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, system, methods, and devices for priming a blood treatment device. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicant intends to embrace all such alternatives, modifications, equivalents, and variations that are within the spirit and scope of the present invention.

The invention claimed is:

1. A method for performing a blood treatment, comprising:
    flowing blood from a patient through an extracorporeal blood treatment system that uses a replaceable blood treatment device;
    detecting a condition indicating a need to replace the replaceable blood treatment device;
    priming a blood treatment device to provide a primed blood treatment device; and
    replacing the replaceable blood treatment device with the primed blood treatment device.

2. The method of claim 1, wherein the detecting includes detecting a change in a pressure of a blood circuit.

3. The method of claim 2, wherein the detecting includes detecting a pressure property indicating a rise in pressure drop through the replaceable blood treatment device.

4. The method of claim 1, wherein the flowing includes performing a hemodialysis, hemofiltration, apheresis, or a type of renal replacement therapy treatment.

5. The method of claim 1, wherein the priming includes creating a siphon flow in a priming circuit and automatically halting the siphon flow prior to an entry of air or other gas or gasses into a fluid circuit of the extracorporeal blood treatment system.

6. The method of claim 5, wherein the automatically halting includes a passive starvation of a flow from a priming source.

7. The method of claim 5, wherein the automatically halting includes a complete filling of a fluid-receiving device until it can hold no further fluid.

8. The method of claim 7, wherein the receiving device includes a drain bag of inelastic material.

9. The method of claim 7, wherein the receiving device includes a drain bag of relatively inelastic and relatively elastic materials bonded as a dual layer film.

10. The method of claim 7, wherein the receiving device includes a drain container with a maximum fill volume that is less than a total volume of fluid of a source container less a volume of the primed blood treatment device less a volume of a priming circuit between the primed blood treatment device and the drain container.

11. The method of claim 10, wherein the drain container is a bilayer bag that includes two layers of film, a first a layer of the two layers of film being stiffer than a second of the two layers of film.

12. The method of claim 1, wherein the replacing includes disconnecting the primed blood treatment device from a priming circuit using self-sealing connectors.

13. The method of claim 1, wherein the priming includes creating a siphon flow in a priming circuit and automatically halting the siphon flow prior to an entry of air or other gas or gasses into a fluid circuit of the extracorporeal blood treatment system, wherein the automatically halting includes a passive starvation of a flow from a priming source by a valve that blocks passage of air or other gas or gasses from a priming source but permits flow of priming fluid.

* * * * *